(12) United States Patent
Li et al.

(10) Patent No.: US 9,556,185 B2
(45) Date of Patent: Jan. 31, 2017

US009556185B2

(54) ORGANIC COMPOUNDS

(75) Inventors: Peng Li, New York, NY (US); Hailin Zheng, New York, NY (US); Jun Zhao, New York, NY (US); Lawrence P. Wennogle, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 609 days.

(21) Appl. No.: 13/701,235

(22) PCT Filed: May 31, 2011

(86) PCT No.: PCT/US2011/038527
§ 371 (c)(1),
(2), (4) Date: Nov. 30, 2012

(87) PCT Pub. No.: WO2011/153129
PCT Pub. Date: Dec. 8, 2011

(65) Prior Publication Data
US 2013/0085123 A1 Apr. 4, 2013

Related U.S. Application Data

(60) Provisional application No. 61/349,952, filed on May 31, 2010.

(51) Int. Cl.
| | | |
|---|---|---|
| *A61K 31/165* | (2006.01) | |
| *A61K 31/573* | (2006.01) | |
| *A61K 31/565* | (2006.01) | |
| *A61K 31/557* | (2006.01) | |
| *A61K 31/519* | (2006.01) | |
| *A61K 31/19* | (2006.01) | |
| *C07D 487/04* | (2006.01) | |
| *C07D 487/14* | (2006.01) | |
| *A61K 45/06* | (2006.01) | |

(52) U.S. Cl.
CPC .......... *C07D 487/14* (2013.01); *A61K 31/165* (2013.01); *A61K 31/19* (2013.01); *A61K 31/519* (2013.01); *A61K 31/557* (2013.01); *A61K 31/565* (2013.01); *A61K 31/573* (2013.01); *A61K 45/06* (2013.01); *C07D 487/04* (2013.01)

(58) Field of Classification Search
CPC ... C07D 487/04; C07D 487/14; A61K 31/165; A61K 31/573; A61K 31/565; A61K 31/557; A61K 31/519; A61K 31/19; A61K 45/06
USPC .................. 514/171, 257, 267; 544/247, 251
See application file for complete search history.

(56) References Cited

U.S. PATENT DOCUMENTS

| | | | |
|---|---|---|---|
| 5,202,328 A | 4/1993 | De Laszlo et al. | |
| 5,294,612 A | 3/1994 | Bacon et al. | |
| 5,393,755 A | 2/1995 | Neustadt et al. | |
| 5,824,683 A | 10/1998 | McKittrick et al. | |
| 5,939,419 A | 8/1999 | Tulshlan | |
| 6,013,621 A | 1/2000 | Nishi et al. | |
| 6,133,273 A | 10/2000 | Gilbert et al. | |
| 6,235,742 B1 | 5/2001 | Bell et al. | |
| 6,492,371 B2 | 12/2002 | Roylance | |
| 6,756,373 B1 | 6/2004 | Allerton et al. | |
| 6,969,719 B2 | 11/2005 | Asberom et al. | |
| 7,153,824 B2 | 12/2006 | Palmer et al. | |
| 7,157,451 B2 | 1/2007 | Atwal et al. | |
| 8,829,008 B2 | 9/2014 | Li et al. | |
| 9,073,936 B2 | 7/2015 | Li et al. | |
| 2003/0069246 A1 | 4/2003 | Darrow et al. | |
| 2003/0092908 A1 | 5/2003 | Pitts et al. | |
| 2003/0162782 A1 | 8/2003 | Grossman et al. | |
| 2005/0075795 A1 | 4/2005 | Pandit | |
| 2005/0113379 A1 | 5/2005 | Ge et al. | |
| 2006/0252790 A1 | 11/2006 | Allen et al. | |
| 2008/0176961 A1 | 7/2008 | Greengard et al. | |
| 2008/0188492 A1 | 8/2008 | Li et al. | |
| 2008/0193964 A1 | 8/2008 | Greengard et al. | |
| 2008/0194592 A1 | 8/2008 | Mates et al. | |
| 2010/0087450 A1 | 4/2010 | Fienberg et al. | |
| 2010/0173878 A1 | 7/2010 | Li et al. | |
| 2010/0273753 A1 | 10/2010 | Li et al. | |
| 2010/0273754 A1 | 10/2010 | Li et al. | |

(Continued)

FOREIGN PATENT DOCUMENTS

| | | |
|---|---|---|
| DE | 19931206 | 1/2001 |
| EP | 0095289 | 11/1983 |

(Continued)

OTHER PUBLICATIONS

Goodman & Gilman, The Pharmacological Basis of Therapeutics, McGraw-Hill Interamericana. 2007, p. 892.
Shook, et al. "Design and Characterization of Optimized Adenoside A$_{2A}$/A$_1$ Receptor Antagonists for the Treatment of Parkinson's Disease", *J. Med. Chem.*, pp. 1-47 (2012).
Aswar, "Anti-Cataleptic Activity of Various Extracts of *Ocimum Sanctum*", International Journal of Pharma. Research and Development, vol. 2, Issue 6, pp. 1-7 (2010).
Boyd et al., "Dopamine receptor signaling and current and future antipsychotic drugs", *Handb Exp Pharmacol.* 2012; (212):53-86. doi:10.1007/978-3-642-25761-2_3.

(Continued)

*Primary Examiner* — Alexander R Pagano
*Assistant Examiner* — Ebenezer O Sackey
(74) *Attorney, Agent, or Firm* — Hoxie & Associates LLC

(57) ABSTRACT

The present invention relates to optionally substituted 4,5,7,8-tetrahydro-(optionally 4-oxo, 4-thioxo or 4-imino)-(1H or 2H)-imidazo[1,2-a]pyrazolo[4,3-e]pyrimidine or 4,5,7,8,9-pentahydro-(optionally 4-oxo, 4-thioxo or 4-imino)-(1H or 2H)-pyrimido[1,2-a]pyrazolo[4,3-e]pyrimidine compounds, and methods of using said compound, e.g., wherein the treatment relates to diseases involving disorders of the dopamine D1 receptor intracellular pathway, such as, among others, Parkinson's disease, depression, narcolepsy, damage to cognitive function, e.g., in schizophrenia.

8 Claims, No Drawings

(56) References Cited

U.S. PATENT DOCUMENTS

| | | |
|---|---|---|
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2013/0018063 A1 | 1/2013 | Li et al. |
| 2013/0239234 A1 | 9/2013 | Greengard et al. |
| 2013/0331363 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1* | 7/2014 | Li et al. .......... 514/171 |
| 2014/0315868 A1 | 10/2014 | Li et al. |
| 2014/0357606 A1 | 12/2014 | Li et al. |
| 2015/0038474 A1 | 2/2015 | Li et al. |
| 2015/0072965 A1 | 3/2015 | Li et al. |
| 2015/0080357 A1 | 3/2015 | Li et al. |
| 2015/0197528 A1 | 7/2015 | Li et al. |
| 2015/0259353 A1 | 9/2015 | Li et al. |
| 2016/0031895 A1 | 2/2016 | Li et al. |
| 2016/0039835 A1 | 2/2016 | Li et al. |
| 2016/0083390 A1 | 3/2016 | Li et al. |

FOREIGN PATENT DOCUMENTS

| | | |
|---|---|---|
| EP | 0201188 | 12/1986 |
| EP | 0636626 | 2/1995 |
| EP | 0911333 | 4/2002 |
| JP | 53031694 | 3/1978 |
| WO | WO 91/19717 | 12/1991 |
| WO | WO 94/19351 | 9/1994 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 2006/133261 | 12/2006 |
| WO | WO 2007/143568 | 12/2007 |
| WO | WO 2007/143705 | 12/2007 |
| WO | WO 2008/063505 | 5/2008 |
| WO | WO 2009/073210 | 6/2009 |
| WO | WO 2009/075784 | 6/2009 |
| WO | WO 2010/065148 | 6/2010 |
| WO | WO 2010/065149 | 6/2010 |
| WO | WO 2010/065151 | 6/2010 |
| WO | WO 2011/043816 | 4/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |
| WO | WO 2013/192556 | 12/2013 |

OTHER PUBLICATIONS

Deshmukh et al., "Amelioration of intracerebroventricular streptozotocin induced cognitive dysfunction and oxidative stress by vinpocetine—a PDE1 inhibitor" *European Journal of Pharmacology* (2009), 620(1-3), 49-56.

Filgueiras et al., "Phosphodiesterase type 1 inhibition improves learning in rats exposed to alcohol during the third trimester equivalent of human gestation" *Neuroscience Letters* (2010), 473(3), 202-207.

Schmidt, "Phosphodiesterase inhibitors as potential cognition enhancing agents" *Current Topics in Medicinal Chemistry* (2010), 10(2), 222-230.

Ehrman et al., "Phosphodiesterase 1B differentially modulates the effects of methamphetamine on locomotor activity and spatial learning through DARPP32-dependent pathways: evidence from PDE1B-DARPP32 double-knockout mice", *Genes Brain Behav.* Oct. 2006;5(7):540-51.

Klaissle, "Physical activity and environmental enrichment regulate the generation of neural precursors in the adult mouse substantia nigra in a dopamine-dependent manner" *BMC Neurosci.* 2012)31;13:132. doi: 10.1186/1471-2202-13-132.

Kleppisch, "Phosphodiesterases in the central nervous system" *Handb Exp Pharmacol.* 2009;(191):71-92. doi: 10.1007/978-3-540-68964-5_5.

Chalimoniuk "Upregulation of guanylyl cyclase expression and activity in striatum of MPTP-induced parkinsonism in mice" *Biochem Biophys Res Commun.* Nov. 5, 2004;324(1):118-26.

Kakkar, et al. "Calmodulin-dependent cyclic nucleotide phosphodiesterase (PDE1)" *Cell Mol Life Sci.* Jul. 1999;55(8-9):1164-86.

Kakkar, et al. "Amantadine: an antiparkinsonian agent inhibits bovine brain 60 kDa calmodulin-dependent cyclic nucleotide phosphodiesterase isozyme", *Brain Res.* Feb. 28, 1997;749(2):290-4.

Hulley et al., "Cyclic AMP promotes the survival of dopaminergic neurons in vitro and protects them from the toxic effects of MPP+" *J Neural Transm Suppl.* (1995); 46:217-28.

Laddha et al., "A new therapeutic approach in Parkinson's disease: Some novel quinazoline derivatives as dual selective phosphodiesterase 1 inhibitors and anti-inflammatory agents" *Bioorganic & Medicinal Chemistry* (2009), 17(19), 6796-6802.

Medina. "Therapeutic Utility of Phosphodiesterase Type 1 Inhibitors in Neurological Conditions", Front. Neurosci. 5: 21, 6 pages, (2011).

Kakkar, et al., "Inhibition of Bovine Brain Calmodulin-Dependent Cyclic Nucleotide Phosphodiesterase Isozymes by Deprenyl", *Life Sciences*, vol. 59, No. 21, pp. 337-341 (1996).

Sharma, et al., "Regulation of Calmodulin-Stimulated Cyclic Nucleotide Phosphodiesterase (PDE1): Review", *International Journal of Molecular Medicine*, 18: 95-105 (2006).

Blokland, "PDE Inhibition and Cognition Enhancement", vol. 22 No. 4, pp. 349-354 (2012) (Abstract Only).

Chen et al., Effects of Bimatoprost 0.03% on Ocular Hemodynamics in Normal Tension Glaucoma; Journal of Ocular Pharmacology nd Therpaeutics, vol. 22, No. 3, 2006.

Noguchi et al; "A Facile Preparation of 7-(substituted amino-)-6H-pyrrolo[3,4-d]-pyrimidine Derivatives"; Bulletin Chem. Soc. of Japan, 62(9), 3043-5; (1989).

Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chem. (1997) 40(14):2196-2210.

Al-Afaleq, E., et al., "Heterocyclic o-Aminonitriles: Preparation of Pyrazolo[3,4-d]-pyrimidines with Modification of the substituents at the 1-position", *Molecules*, 6, pp. 621-638, (2001).

"Anxiety," [retrieved on May 14, 2008]. Retrieved online via Internet, URL: http://www.nim.nih.gov/medlineplus/anxiety.html.

"Autism," [retrieved on May 14, 2008]. Retrieved online via Internet, URL: http://www.nim.nih.gov/medlineplus/autism.html.

Banker, Gilbert S. et al., Modem Pharmaceutics, Marcel Dekker, New York, 1996.

Bender et al., "Cyclic Nucleotide Phosphodiesterases: Molecular Regulation to Clinical Use" PharmcoL Rev., 2006, 58, pp. 488-520.

Chebib et al., 1-Phenylpyrazolo[3,4-d]pyrimidines; Structure-Activity Relationships for C6 Substituents at $A_1$ and $A_{2A}$ Adenosine Receptors Bioorganic & Medicinal Chemistry (2000) 8:2581-2590.

Dewald et al., Synthesis and Potential Antipsychotic Activity of 1 H-Imidazo[1.2-c]pyrazolo[3,4-e]pyrimidines', J. Med. Chem. 1988, 31, pp. 454-461.

Fienberg et al., "DARPP-32: Regulator of the Efficacy of Dopaminergic Neurotransmission", Science, (1998) 281, pp. 838-842.

Gelbin, et al., "Ketene-S, N-acetals as synthons for heterocycles new synthesis of pyrimidinones", *Journal Fuer Praktische Chemie*, vol. 329, No. 5, pp. 753-766, (1987).

(56) References Cited

OTHER PUBLICATIONS

Greengard et al., "Beyond the Dopamine Receptor: the DARPP-321Protein Phosphatase-1 Cascade", Neuron, 1999,23, pp. 435,447.
Han et al., "The Calcium/Calmodulin-dependent Phosphodiesterase PDE1C Downregulates Glucose-induced Insulin Secretion", J. Bio, Chem., 1999,274(32), pp. 22337-22344.
Jiang, et al., Chernoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol, J. Org. Chem., 70, 2824-2827 (2004).
Mani et al., Science (2000) 287: 1053.
Murray et al., "Expression and activity of cAMP phosphodiesterase isoforms in pulmonary artery smooth muscle cells from patients with pulmonary hypertension: role for PDE1", Am. J. Physiol. Lunr:l Cell Mol. Physiol. 2007, 292, pp. L294-L303.
Nishi, A., et al., "Advanced Research on Dopamine Signaling to Develop Drugs for the Treatment of Mental Disorders: Biochemical and Behavioral Profiles of Phosphodiesterase Inhibition in Dopaminergic Neurotransmission", J. Pharmacol. Sci. vol. 114, pp. 6-16, (2010).
Polli et al., "Expression of a Calmodulin-Dependent Phosphodiesterase Isoform (PDE1 B1) Correlates With Brain Regions Having Extensive Dopaminergic Innervation," (1994), The Journal of Neuroscience, 14:1251-1261.
Porsolt et al. Nature (1977) 266:730-732.
Poulsen et al.HIgh-Pressure Synthesis of Enantiomerlcally Pure C-6 Substituted Pyrazolo[3,4-d]pyrimidines Biorganic & Medicinal Chemistry letter (2001) 11:191-193.
Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning", The Joumal of Neuroscience, 2002, 22(12), pp. 5188-5197.
Rybalkin et al., "Cyclic GMP Phosphodiesterases and Regulation of Smooth Muscle Function", Circ. Res. 2003,93, pp. 280-291.
Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium", Cancer Research, 2004, 64, pp. 2568-2571.
Turko et al., Inhibition of Cyclic GMP-Binding Cyclic GMP-Specific Phosphodiesterase (Type 5) by Sildenafil and Related Compounds Molecular Pharmacology (1990) 56:124-130.
Vatter, et al., Differential Phosphodiesterase Expression and Cytosolic Ca2+ in Human CNS Tumour Cells and in Non-Malignant and Malignant Cells of Rat Origin, J. of Neurochemistry, 93, 321-329 (2005).
Wolff, Manfred E., Burger's Medicinal Chemistry and Drug Discovery, Fifth Ed., vol. 1: Principles and Practice, John Wiley & Sons, 1995, 975.
Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).
Ennaceur et al., "A New One-Trial Test for Neurobiological Studies of Memory in Rats. 1:Behavioral Data", Behavioural Brain Research, 1988, 31:47-59.
Ghorab et al., Synthesis, anticancer and radioprotective activities of some new pyrazolo[3,4-d]pyrimidines containing amino acid moieties, Arzneimittel Forschung, 2009, 59(2):96-103.
Patani et al., "Bioisosterism: A Rational Approach in Drug Design", Chem. Rev., 1996, 96:3147-3176.
Prickaerts et al., "Possible Role of Nitric Oxide-Cyclic GMP Pathway in Object Recognition Memory: Effects of 7-Nitroindazole and Zaprinast", European Journal of Pharmacology, 1997, 337:125-136.
Pardo, et al., "Synthesis of 1-(p-nitrobenzyl)azoles and 1-(p-nitrobenzyl)benzazoles", Opp Briefs, 2000, 32(4):385-390.
Takimoto, "Controlling Myocyte cGMP: Phosphodiesterase 1 Joins the Fray," Circ Res., 2009, 105(10):931-933.
Wermuth, "Molecular Variations based on isosteric replacements" The Practice of Chemistry, Technomics, Inc., Aug. 1998, 1(13): 235-271.
Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.

\* cited by examiner

ORGANIC COMPOUNDS

CROSS REFERENCE TO RELATED APPLICATIONS

This application is a United States Application under 35 U.S.C. 371 claiming benefit of PCT Application No. PCT/US2011/038527, filed on May 31, 2011, which claims priority from U.S. Provisional Application No. 61/349,952, filed on May 31, 2010, the contents of each of which are hereby incorporated by reference in their entirety.

TECHNICAL FIELD

The present invention relates to optionally substituted 4,5,7,8-tetrahydro-(optionally 4-oxo, 4-thioxo or 4-imino)-(1H or 2H)-imidazo[1,2-a]pyrazolo[4,3-e]pyrimidine or 4,5,7,8,9-pentahydro-(optionally 4-oxo, 4-thioxo or 4-imino)-(1H or 2H)-pyrimido[1,2-a]pyrazolo[4,3-e]pyrimidine compounds, preferably Compounds of Formula I as described below, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as, among others, Parkinson's disease, depression, narcolepsy, damage to cognitive function, e.g., in schizophrenia, or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5' AMP and 5' GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1A and/or PDE1B activity.

SUMMARY OF THE INVENTION

The invention provides optionally substituted 4,5,7,8-tetrahydro-(optionally 4-oxo, 4-thioxo or 4-imino)-(1H or 2H)-imidazo[1,2-a]pyrazolo[4,3-e]pyrimidine or 4,5,7,8,9-pentahydro-(optionally 4-oxo, 4-thioxo or 4-imino)-(1H or 2H)-pyrimido[1,2-a]pyrazolo[4,3-e]pyrimidine compounds, in free or salt form, e.g., optionally substituted:
4,5,7,8-tetrahydro-(1H or 2H)-imidazo[1,2-a]pyrazolo[4,3-e]pyrimidine, 4,5,7,8-tetrahydro-(1H or 2H)-imidazo[1,2-a]pyrazolo[4,3-e]pyrimidine-4(5H)-one, 4,5,7,8-tetrahydro-(1H or 2H)-imidazo[1,2-a]pyrazolo[4,3-e]pyrimidine-4(5H)-thione, 4,5,7,8-tetrahydro-(1H or 2H)-imidazo[1,2-a]pyrazolo[4,3-e]pyrimidine-4(5H)-imine, 4,5,7,8,9-pentahydro-(1H or 2H)-pyrimido[1,2-a]pyrazolo[4,3-e]pyrimidine, 4,5,7,8,9-pentahydro-(1H or 2H)-pyrimido[1,2-a]pyrazolo[4,3-e]pyrimidine-4(5H)-one, 4,5,7,8,9-pentahydro-(1H or 2H)-pyrimido[1,2-a]pyrazolo[4,3-e]pyrimidine-4(5H)-thione, 4,5,7,8,9-pentahydro-(1H or 2H)-pyrimido[1,2-a]pyrazolo[4,3-e]pyrimidine-4(5H)-imine, in free or salt form, preferably (1 or 2 and/or 3 and/or 5) substituted, more preferably with 3-oxy-substituted compounds.

In another embodiment, the invention provides a Compound of Formula I:

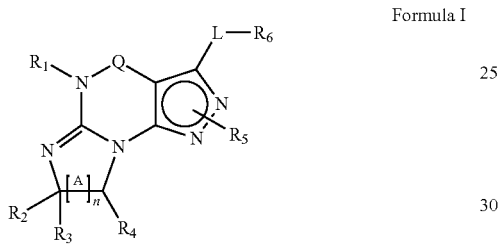

Formula I wherein
(i) Q is —C(=S)—, —C(=N($R_{20}$))—, —C(=O)— or $CH_2$;
(ii) L is a —O—;
(iii) $R_1$ is H or $C_{1-4}$alkyl (e.g., methyl or ethyl);
(iv) $R_4$ is H or $C_{1-4}$alkyl (e.g., methyl or isopropyl) and $R_2$ and $R_3$ are, independently:
  H,
  $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
  aryl,
  heteroaryl,
  (optionally hetero)aryl$C_{1-6}$alkyl, or
  $R_2$ and $R_3$ together with the carbon to which they are attached form a 3- to 6-membered ring; or
  $R_2$ is H and $R_3$ and $R_4$ together form a di-, tri- or tetra-methylene bridge,
  (pref. wherein the $R_3$ and $R_4$ together have the cis configuration, e.g., where the carbons carrying $R_3$ and $R_4$ have the R and S configurations, respectively);
(v) $R_5$ is
  a) -D-E-F, wherein:
    D is a single bond, $C_{1-4}$alkylene (e.g., methylene, ethylene or prop-2-yn-1-ylene) or —C(=O)—;
    E is a single bond, $C_{1-4}$alkylene (e.g., methylene, —C≡C—), arylene (e.g., phenylene), aryl$C_{1-4}$alkylene (e.g., benzylene) or heteroarylene (e.g., pyridylene); and
    F is
      H,
      aryl (e.g., phenyl),
      heteroaryl (e.g., pyridyl, diazolyl, triazolyl, for example, pyrid-2-yl, imidazol-1-yl, pyrazol-1-yl, 1,2,4-triazol-1-yl),
      halo (e.g., F, Br, Cl),
      $C_{1-4}$alkyl (e.g., methyl),
      halo$C_{1-4}$alkyl (e.g., trifluoromethyl),
      halo$C_{1-4}$alkoxy,
      $C_{1-4}$alkoxy (e.g., methoxy),
      —C(O)—$R_{15}$,
      —N($R_{16}$)($R_{17}$),
      —S(O)$_2R_{21}$,
      $C_{3-7}$cycloalkyl (e.g., cyclopentyl or cyclohexyl), or hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl);
    wherein D, E and F are independently and optionally substituted with one or more group selected from:
      halo (e.g., F, Cl or Br),
      $C_{1-4}$alkyl (e.g., methyl or prop-2-yn-1-yl), halo$C_{1-4}$alkyl (e.g., trifluoromethyl), and $C_{1-4}$alkoxy (methoxy),
    for example, F is heteroaryl (e.g., pyridyl (for example pyrid-2-yl, pyrid-3-yl, pyrid-4-yl), thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl or oxadiazolyl (e.g., 1,2,4-oxodiazol-3-yl) optionally substituted with one or more group selected from halo and $C_{1-6}$alkyl (e.g., 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl),
    or F is aryl, e.g., phenyl, optionally substituted with one or more halo (e.g., 4-fluorophenyl);
    or F is a $C_{3-7}$heterocycloalkyl (e.g., pyrrolidinyl) optionally substituted with a $C_{1-6}$alkyl (e.g., 1-methylpyrrolidin-3-yl, 1-methylpyrrolidin-2-yl, 1-ethylpiperidin-1-yl or 1-methylpiperidin-2-yl);
  b) a substituted heteroaryl$C_{1-4}$alkyl, e.g., substituted with halo$C_{1-4}$alkyl;
  or
  c) attached to one of the nitrogen atoms on the pyrazolo portion of Formula I and is a moiety of Formula A

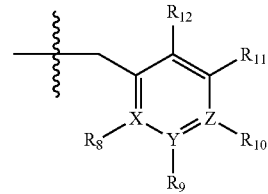

Formula A wherein X, Y and Z are, independently, N or C, and $R_8$, $R_9$, $R_{11}$ and $R_{12}$ are independently H, halogen (e.g., Cl or F), —$C_{1-4}$alkyl-N($R_{22}$)($R_{23}$) (e.g., aminomethyl, isopropylaminomethyl or isobutylaminomethyl), or —$C_{1-4}$alkyl-heter$C_{3-8}$cycloalkyl (e.g., pyrrolidin-1-ylmethyl), and $R_{10}$ is:
  hydrogen,
  halogen (chloro or fluoro),
  $C_{1-4}$alkyl,
  halo$C_{1-4}$alkyl (e.g., trifluoromethyl), halo$C_{1-4}$alkoxy (e.g., trifluoromethoxy), $C_{1-4}$alkoxy,
$C_{3-7}$cycloalkyl,
het$C_{3-7}$cycloalkyl (e.g., pyrrolidinyl or piperidinyl, for example piperidin-2-yl or pyrrolidin-2-yl),
$C_{1-4}$haloalkyl (e.g., trifluoromethyl),
aryl (e.g., phenyl),
heteroaryl (e.g., pyridyl (for example pyrid-2-yl, pyrid-3-yl, pyrid-4-yl), thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl or oxodiazolyl (e.g., 1,2,4-oxodiazol-3-yl),
arylcarbonyl (e.g., benzoyl),
$C_{1-4}$alkylsulfonyl (e.g., methylsulfonyl),
aminosulfonyl (e.g., —S(O)$_2$—N(R$_{18}$)(R$_{19}$),
heteroarylcarbonyl,
$C_{1-4}$alkylcarbonyl (e.g., methylcarbonyl),
$C_{1-4}$alkoxycarbonyl, (e.g., —C(O)OCH$_3$),
—C(O)OH,
halo$C_{1-4}$alkoxycarbony (e.g., trifluoromethylcarbonyl),
—C(O)N(R$_{18}$)(R$_{19}$), or
—C$_{1-4}$alkyl-N(R$_{18}$)(R$_{19}$) (e.g., methylaminomethyl),
wherein the aryl, heteroaryl, cycloalkyl and heterocycloalkyl are independently and optionally substituted with one or more group selected from halo (e.g., F or Cl), $C_{1-4}$alkyl (e.g., methyl or prop-2-yn-1-yl), $C_{1-4}$alkoxy, $C_{1-4}$haloalkyl (e.g., trifluoromethyl) and —SH;
For example, R$_{10}$ is phenyl, pyridyl, pyrazolyl, piperidinyl, pyrrolidinyl oxadiazolyl pyrimidinyl, optionally substituted with one or more group selected from halo (e.g., F or Cl), $C_{1-4}$alkyl (e.g., methyl or prop-2-yn-1-yl), $C_{1-4}$alkoxy, $C_{1-4}$haloalkyl (e.g., trifluoromethyl) and —SH, e.g. optionally substituted with halo or $C_{1-4}$alkyl, for example R$_{10}$ is 1-methylpiperidin-2-yl, piperidin-2-yl, 1-ethylpiperidin-2-yl, 1-methylpyrrolidin-2-yl, 1-methylimidazol-2-yl, halopyridyl (for example 6-fluoropyrid-2-yl),
provided that when X, Y, or Z is nitrogen, R$_8$, R$_9$, or R$_{10}$, respectively, is not present;
(vi) R$_6$ is
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl), or
aryl$C_{1-4}$alkyl (e.g., benzyl),
wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, R$_6$ is 3-chlorophenyl or 4-fluorophenyl,
(vii) n=0 or 1;
(viii) when n=1, A is —C(R$_{13}$R$_{14}$)—, wherein R$_{13}$ and R$_{14}$, are, independently, H, $C_{1-4}$alkyl, aryl, heteroaryl, (optionally hetero)aryl$C_{1-4}$alkoxy or (optionally hetero)aryl$C_{1-4}$alkyl or R$_{13}$ or R$_{14}$ can form a di-, tri- or tetramethylene bridge with R$_2$ or R$_4$;
(ix) R$_{15}$ is $C_{1-4}$alkyl (e.g., methyl), halo$C_{1-4}$alkyl (e.g., trifluoromethyl), —OH, —O$C_{1-4}$alkyl (e.g., —OCH$_3$), aryl (e.g., phenyl) or —N(R$_{16}$)(R$_{17}$);
(x) R$_{16}$ and R$_{17}$ are independently H or $C_{1-4}$alkyl;
(xi) R$_{18}$ and R$_{19}$ are independently
H,
$C_{1-4}$alky,
$C_{3-8}$cycloalkyl,
heteroC$_{3-8}$cycloalkyl,
aryl (e.g., phenyl), or
heteroaryl,
wherein said aryl or heteroaryl is optionally substituted with one or more group selected from:
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$alkyl,
halo$C_{1-6}$alkyl,
$C_{1-6}$alkoxy,
aryl,
heteroaryl, and
$C_{3-8}$cycloalkyl;
(xii) R$_{20}$ is H, $C_{1-4}$alkyl (e.g., methyl) or $C_{3-7}$cycloalkyl;
(xiii) R$_{21}$ is $C_{1-6}$alkyl (e.g., methyl) or —N(R$_{18}$)(R$_{19}$);
(xiv) R$_{22}$ and R$_{23}$ are independently H or $C_{1-4}$alkyl (e.g., methyl),
in free or salt form.

In another embodiment, the invention provides a Compound of Formula I as follows:

1.1 Formula I, wherein Q is —C(=S)—, —C(=N(R$_{20}$))—, —C(=O)— or CH$_2$;
1.2 Formula I or 1.1, wherein Q is —C(=S)—;
1.3 Formula I or 1.1, wherein Q is —C(=O)—
1.4 Formula I or 1.1, wherein Q is —C(=N(R$_{20}$))—;
1.5 Formula I or 1.1, wherein Q is —CH$_2$—;
1.6 Formula I, or any of 1.1-1.5, wherein R$_1$ is H or $C_{1-4}$alkyl (e.g., methyl or ethyl);
1.7 Formula 1.6, wherein R$_1$ is H,
1.8 Formula 1.6, wherein R$_1$ is $C_{1-4}$alkyl (e.g., methyl or ethyl);
1.9 Formula I, or any of 1.1-1.8, wherein R$_4$ is H or $C_{1-4}$alkyl (e.g., methyl, isopropyl) and R$_2$ and R$_3$ are, independently:
H,
$C_{1-6}$alkyl (e.g., methyl or isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)aryl$C_{1-6}$alkoxy,
(optionally hetero)aryl$C_{1-6}$alkyl, or
R$_2$ and R$_3$ together with the carbon to which they are attached form a 3- to 6-membered ring;
or
R$_2$ is H and R$_3$ and R$_4$ together form a di-, tri- or tetramethylene bridge,
(pref. wherein the R$_3$ and R$_4$ together have the cis configuration, e.g., where the carbons carrying R$_3$ and R$_4$ have the R and S configurations, respectively)
1.10 Formula 1.9, wherein R$_2$ or R$_3$ is H or $C_{1-6}$alkyl (e.g., methyl or isopropyl);
1.11 Formula 1.9, wherein R$_2$ or R$_3$ is H,
1.12 Formula 1.9, wherein R$_2$ or R$_3$ is $C_{1-6}$alkyl (e.g., methyl or isopropyl);
1.13 Formula 1.9, wherein R$_2$ or R$_3$ is methyl;
1.14 Formula 1.9, wherein R$_2$ or R$_3$ is isopropyl;
1.15 Formula I, or any of 1.1-1.8, wherein R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
1.16 Formula I or any of 1.1-1.15, wherein R$_5$ is -D-E-F;

1.17 Formula 1.16, wherein D is a single bond, $C_{1-4}$alkylene (e.g., methylene, ethylene or prop-2-yn-1-ylene) or —C(=O)—;
1.18 Formula 1.17, wherein D is a single bond;
1.19 Formula 1.17, wherein D is $C_{1-4}$alkylene (e.g., methylene, ethylene or prop-2-yn-1-ylene);
1.20 Formula 1.17, wherein D is methylene;
1.21 Any of formulae 1.16-1.20, wherein E is a single bond, $C_{1-4}$alkylene (e.g., methylene, —C≡C—), arylene (e.g., phenylene), aryl$C_{1-4}$alkylene (e.g., benzylene) or heteroarylene (e.g., pyridylene);
1.22 Any of formulae 1.16-1.20, wherein E is arylene (e.g., phenylene);
1.23 Any of formulae 1.16-1.20, wherein E is phenylene;
1.24 Any of formulae 1.16-1.20, wherein E is heteroarylene (e.g., pyridylene);
1.25 Any of formulae 1.16-1.20, wherein E is $C_{1-4}$alkylene (e.g., methylene, —C≡C—);
1.26 Any of formulae 1.16-1.20, wherein E is aryl$C_{1-4}$alkylene (e.g., benzylene);
1.27 Any of formulae 1.16-1.20, wherein E is a single bond;
1.28 Any of formulae 1.16-1.27, wherein F is
H,
aryl (e.g., phenyl),
heteroaryl (e.g., pyridyl, diazolyl, triazolyl, for example, pyrid-2-yl, pyrid-4-yl, pyrid-3-yl, imidazol-1-yl, pyrazol-1-yl, 1,2,4-triazol-1-yl),
halo (e.g., F, Br, Cl),
halo$C_{1-4}$alkyl (e.g., trifluoromethyl),
halo$C_{1-4}$alkoxy,
$C_{1-4}$alkoxy (e.g., methoxy),
—C(O)—$R_{15}$,
—N($R_{16}$)($R_{17}$),
—S(O)$_2R_{21}$,
$C_{3-7}$cycloalkyl (e.g., cyclopentyl or cyclohexyl), or
hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl);
wherein F is optionally substituted with one or more group selected from:
halo (e.g., F, Cl or Br),
$C_{1-4}$alkyl (e.g., methyl or prop-2-yn-1-yl),
halo$C_{1-4}$alkyl (e.g., trifluoromethyl),
$C_{1-4}$alkoxy, and
$C_{1-4}$alkyl (e.g., 5-methylpyrid-2-yl),
for example, F is heteroaryl (e.g., pyridyl, pyrazolyl or imidazolyl), aryl (e.g., phenyl) or hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl), optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy) or $C_{1-4}$alkyl (for example, F is 5-methylpyrid-2-yl, 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl, 4-fluorophenyl, 1-methylpyrrolidin-3-yl, 1-methylpyrrolidin-2-yl, 1-ethylpiperidin-1-yl or 1-methylpiperidin-2-yl);
1.29 Formula 1.28, wherein F is H;
1.30 Formula 1.28, wherein F is halo$C_{1-4}$alkyl (e.g., trifluoromethyl);
1.31 Formula 1.28, wherein F is trifluoromethyl;
1.32 Formula 1.28, wherein F is halo (e.g., F, Br or Cl);
1.33 Formula 1.28, wherein F is Cl;
1.34 Formula 1.28, wherein F is heteroaryl (e.g., pyridyl (for example pyrid-2-yl, pyrid-3-yl, pyrid-4-yl), or thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl or oxadiazolyl (e.g., 1,2,4-oxodiazol-3-yl) optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy or $C_{1-4}$alkyl, (e.g., 5-trifluoromethylpyrid-2-yl, 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl);
1.35 Formula 1.28, wherein F is heteroaryl (e.g., pyridyl, diazolyl, triazolyl, for example, pyrid-2-yl, pyrid-4-yl, pyrid-3-yl, imidazol-1-yl, pyrazol-1-yl, 1,2,4-triazol-1-yl) optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy) or $C_{1-4}$alkyl;
1.36 Any Formulae 1.34-1.35, wherein F is pyrid-2-yl (e.g., pyrid-2-yl, pyrid-3-yl, pyrid-4-yl);
1.37 Formula 1.34, wherein F is pyridyl (e.g., pyrid-2-yl, pyrid-3-yl, pyrid-4-yl) optionally substituted with one or more halo (e.g., phenyl, 4-fluorophenyl or 3-chlorophenyl);
1.38 Formula 1.34 or 1.37, wherein F is 6-fluoropyrid-2-yl;
1.39 Formula 1.34 or 1.37, wherein F is 3-fluoropyrid-2-yl;
1.40 Formula 1.34 or 1.37, wherein F is 4-fluoropyrid-2-yl;
1.41 Formula 1.34, wherein F is 5-fluoropyrid-2-yl;
1.42 Formula 1.34, wherein F is 5-trifluoromethylpyrid-2-yl;
1.43 Formula 1.34, wherein F is 5-methylpyrid-2-yl;
1.44 Formula 1.34, wherein F is 6-thio-pyrid-2-yl;
1.45 Formula 1.34, wherein F is 1,2,4-triazolyl (e.g., 1,2,4-triazolyl);
1.46 Any Formulae 1.34-1.35, wherein F is diazolyl (e.g., imidazol-1-yl or pyrazol-1-yl);
1.47 Formula 1.34, wherein F is imidazol-1-yl or pyrazol-1-yl;
1.48 Formula 1.34, wherein F is aryl (e.g., phenyl) optionally substituted with one or more:
halo (e.g., F, Cl or Br),
$C_{1-4}$alkyl (e.g., methyl or prop-2-yn-1-yl),
halo$C_{1-4}$alkyl (e.g., trifluoromethyl),
$C_{1-4}$alkoxy or
$C_{1-4}$alkyl (e.g., 5-methylpyrid-2-yl);
1.49 Formula 1.34 or 1.47, wherein F is phenyl optionally substituted with the substituents set forth in formula 1.47;
1.50 Formula 1.34 or 1.47, wherein F is 4-fluorophenyl or 3-chlorophenyl;
1.51 Formula 1.34, wherein F is $C_{3-7}$cycloalkyl (e.g., cyclopentyl, cyclohexyl) optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy or $C_{1-4}$alkyl;
1.52 Formula 1.51, wherein F is cyclohexyl;
1.53 Formula 1.51, wherein F is cyclopentyl;
1.54 Formula 1.28, wherein F is hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl)

optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy or $C_{1-4}$alkyl;

1.55 Formula 1.54, wherein F is pyrrolidinyl (e.g., pyrrolidin-3-yl, pyrrolidin-2-yl or pyrrolidin-1-yl) optionally substituted with one or more $C_{1-4}$alkyl;

1.56 Formula 1.54, wherein F is 1-methylpyrrolidinyl or 1-ethylpyrrolidinyl;

1.57 Formula 1.54, wherein F is piperidinyl (e.g., piperidin-2-yl) optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy or $C_{1-4}$alkyl;

1.58 Formula 1.54 or 1.57, wherein F is piperidinyl (e.g., piperidin-2-yl) optionally substituted with $C_{1-4}$alkyl (e.g., methyl or prop-2-yn-1-yl);

1.59 Formula 1.54 or 1.57, wherein F is 1-methylpiperidin-2-yl or 1-ethylpiperidin-2-yl;

1.60 Formula 1.54, wherein F is tetrahydro-2H-pyran-4-yl;

1.61 Formula 1.28, wherein F is aryl (e.g., phenyl) optionally substituted with one or more halo (e.g., F, Cl or Br), $C_{1-4}$alkyl (e.g., methyl or prop-2-yn-1-yl), halo$C_{1-4}$alkyl (e.g., trifluoromethyl), $C_{1-4}$alkoxy or $C_{1-4}$alkyl;

1.62 Formula 1.61, wherein F is phenyl;

1.63 Formula 1.61, wherein F is 4-fluorophenyl;

1.64 Formula 1.28, wherein F is —S(O)$_2$R$_{21}$ wherein R$_{21}$ is $C_{1-6}$alkyl (e.g., methyl) or —N(R$_{18}$)(R$_{19}$);

1.65 Formula 1.64, wherein R$_{21}$ is $C_{1-6}$alkyl (e.g., methyl);

1.66 Formula 1.64, wherein R$_{21}$ is —N(R$_{18}$)(R$_{19}$);

1.67 Formula 1.28, wherein F is —C(O)—R$_{15}$ and R$_{15}$ is $C_{1-4}$alkyl (e.g., methyl), halo$C_{1-4}$alkyl (e.g., trifluoromethyl), —OH, —O$C_{1-4}$alkyl (e.g., —OCH$_3$), aryl (e.g., phenyl) or —N(R$_{16}$)(R$_{17}$);

1.68 Formula 1.28, wherein F is —C(O)—R$_{15}$ and R$_{15}$ is $C_{1-4}$alkyl (e.g., methyl), halo$C_{1-4}$alkyl (e.g., trifluoromethyl), —OH, —O$C_{1-4}$alkyl (e.g., —OCH$_3$), aryl (e.g., phenyl) or —N(R$_{16}$)(R$_{17}$);

1.69 Formula 1.68, wherein R$_{15}$ is $C_{1-4}$alkyl (e.g., methyl);

1.70 Formula 1.68, wherein R$_{15}$ is halo$C_{1-4}$alkyl (e.g., trifluoromethyl);

1.71 Formula 1.68, wherein R$_{15}$ is —OH;

1.72 Formula 1.68, wherein R$_{15}$ is —O$C_{1-4}$alkyl (e.g., methoxy or ethoxy);

1.73 Formula 1.68, wherein R$_{15}$ is ethoxy;

1.74 Formula 1.28, wherein F is —N(R$_{16}$)(R$_{17}$);

1.75 Any of formulae 1.16-1.74, wherein D, E and F are independently and optionally substituted with one or more:
halo (e.g., F, Cl or Br),
$C_{1-4}$alkyl (e.g., methyl or prop-2-yn-1-yl),
halo$C_{1-4}$alkyl (e.g., trifluoromethyl), or
$C_{1-4}$alkoxy (methoxy);

1.76 Formula I or any of 1.1-1.15, wherein R$_5$ is a substituted heteroarylalkyl, e.g., substituted with haloalkyl;

1.77 Formula I or any of 1.1-1.15, wherein R$_5$ is attached to one of the nitrogen atoms on the pyrazolo portion of Formula I and is a moiety of Formula A

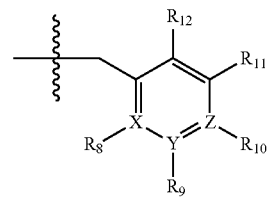

Formula A wherein X, Y and Z are, independently, N or C, and R$_8$, R$_9$, R$_{11}$ and R$_{12}$ are independently H, halogen (e.g., Cl or F), —$C_{1-4}$alkyl-N(R$_{22}$)(R$_{23}$) (e.g., aminomethyl, isopropylaminomethyl or isobutylaminomethyl), or —$C_{1-4}$alkyl-heterC$_{3-8}$cycloalkyl (e.g., pyrrolidin-1-ylmethyl), and R$_{10}$ is:
hydrogen,
halogen (chloro or fluoro),
$C_{1-4}$alkyl,
halo$C_{1-4}$alkyl (e.g., trifluoromethyl),
halo$C_{1-4}$alkoxy (e.g., trifluoromethoxy),
$C_{1-4}$alkoxy,
$C_{3-7}$cycloalkyl,
hetC$_{3-7}$cycloalkyl (e.g., pyrrolidinyl or piperidinyl, for example piperidin-2-yl or pyrrolidin-2-yl),
$C_{1-4}$haloalkyl (e.g., trifluoromethyl),
aryl (e.g., phenyl),
heteroaryl (e.g., pyridyl (for example pyrid-2-yl, pyrid-3-yl, pyrid-4-yl), thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl or oxodiazolyl (e.g., 1,2,4-oxodiazol-3-yl),
arylcarbonyl (e.g., benzoyl),
$C_{1-4}$alkylsulfonyl (e.g., methylsulfonyl),
aminosulfonyl (e.g., —S(O)$_2$—N(R$_{18}$)(R$_{19}$),
heteroarylcarbonyl,
$C_{1-4}$alkylcarbonyl (e.g., methylcarbonyl),
$C_{1-4}$alkoxycarbonyl, (e.g., —C(O)OCH$_3$),
—C(O)OH,
halo$C_{1-4}$alkoxycarbony (e.g., trifluoromethylcarbonyl),
—C(O)N(R$_{11}$)(R$_{19}$), or
—$C_{1-4}$alkyl-N(R$_{18}$)(R$_{19}$) (e.g., methylaminomethyl),
wherein the aryl, heteroaryl, cycloalkyl and heterocycloalkyl are independently and optionally substituted with one or more group selected from halo (e.g., F or Cl), $C_{1-4}$alkyl (e.g., methyl or prop-2-yn-1-yl), $C_{1-4}$alkoxy, $C_{1-4}$haloalkyl (e.g., trifluoromethyl) and —SH;
For example, R$_{10}$ is phenyl, pyridyl, pyrazolyl, piperidinyl, pyrrolidinyl oxadiazolyl pyrimidinyl, optionally substituted with one or more group selected from halo (e.g., F or Cl), $C_{1-4}$alkyl (e.g., methyl or prop-2-yn-1-yl), $C_{1-4}$alkoxy, $C_{1-4}$haloalkyl (e.g., trifluoromethyl) and —SH, e.g. optionally substituted with halo or $C_{1-4}$alkyl, for example R$_{10}$ is 1-methylpiperidin-2-yl, piperidin-2-yl, 1-ethylpiperidin-2-yl, 1-methylpyrrolidin-2-yl, 1-methylimidazol-2-yl, halopyridyl (for example 6-fluoropyrid-2-yl),
provided that when X, Y, or Z is nitrogen, R$_8$, R$_9$, or R$_{10}$, respectively, is not present;

1.78 Formula 1.77, wherein R$_5$ is a substituted heteroarylmethyl, e.g., para-substituted with haloalkyl;

1.79 Formula 1.77, wherein $R_5$ is a moiety of Formula A wherein $R_8$, $R_9$, $R_{11}$, and $R_{12}$ are H and $R_{10}$ is phenyl;

1.80 Formula 1.77, wherein $R_5$ is a moiety of Formula A wherein $R_8$, $R_9$, $R_{11}$, and $R_{12}$ are H and $R_{10}$ is pyridyl or thiadiazolyl;

1.81 Formula 1.77, wherein $R_5$ is a moiety of Formula A wherein $R_8$, $R_9$, $R_{11}$, and $R_{12}$ are, independently, H or halogen, and $R_{10}$ is haloalkyl;

1.82 Formula 1.77, wherein $R_5$ is a moiety of Formula A wherein $R_8$, $R_9$, $R_{11}$, and $R_{12}$ are, independently, H, and $R_{10}$ is alkyl sulfonyl;

1.83 Formula I or any of 1.1-1.82, wherein $R_6$ is
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl), or
aryl$C_{1-4}$alkyl (e.g., benzyl),
wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl;

1.84 Formula 1.83, wherein $R_6$ is $C_{1-4}$alkyl (e.g., isopropyl);

1.85 Formula 1.83, wherein $R_6$ is $C_{3-7}$cycloalkyl (e.g., cyclopentyl or cyclohexyl);

1.86 Formula 1.83, wherein $R_6$ is heteroaryl (e.g., pyridyl, for example, pyrid-4-yl);

1.87 Formula 1.83, wherein $R_6$ is aryl$C_{1-4}$alkyl (e.g., benzyl);

1.88 Formula 1.83, wherein $R_6$ is aryl (e.g., phenyl) optionally substituted with one or more group selected from halo (e.g., F, Cl), hydroxy, $C_{1-6}$alkyl, $C_{1-6}$alkoxy and $C_{3-8}$cycloalkyl;

1.89 Formula 1.83, wherein $R_6$ is fluorophenyl (e.g., 4-fluorophenyl);

1.90 Formula I or any of 1.1-1.89, wherein n=0;

1.91 Formula I or any of 1.1-1.89, wherein n=1;

1.92 Formula 1.91, wherein n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy or (optionally hetero)aryl$C_{1-4}$alkyl;

1.93 Formula I or any of 1.1-1.92, wherein $R_{16}$ and $R_{17}$ are independently H or $C_{1-4}$alkyl;

1.94 formula 1.93, wherein $R_{16}$ and $R_{17}$ are H, 1.95 formula 1.93, wherein $R_{16}$ and $R_{17}$ are $C_{1-4}$alkyl;

1.96 formula 1.93, wherein $R_{16}$ is H and $R_{17}$ is $C_{1-4}$alkyl;

1.97 Formula I or any of 1.1-1.96, wherein $R_{18}$ and $R_{19}$ are independently
H,
$C_{1-4}$alky,
$C_{3-8}$cycloalkyl,
hetero$C_{3-8}$cycloalkyl,
aryl (e.g., phenyl), or
heteroaryl,
wherein said aryl or heteroaryl is optionally substituted with one or more group selected from:
halo (e.g., fluorophenyl, e.g., 4-fluorophenyl),
hydroxy (e.g., hydroxyphenyl, e.g., 4-hydroxyphenyl or 2-hydroxyphenyl),
$C_{1-6}$alkyl,
halo$C_{1-6}$alkyl,
$C_{1-6}$alkoxy,
aryl,
heteroaryl, and
$C_{3-8}$cycloalkyl;

1.98 Formula I or any of 1.1-1.97, wherein $R_{18}$ and $R_{19}$ are independently H or $C_{1-4}$alkyl (e.g., methyl);

1.99 Formula I or any of 1.1-1.98, wherein $R_{20}$ is H, $C_{1-4}$alkyl (e.g., methyl) or $C_{3-7}$cycloalkyl;

1.100 Formula 1.99, wherein $R_{20}$ is H, 1.101 Formula 1.99, wherein $R_{20}$ is $C_{1-4}$alkyl (e.g., methyl);

1.102 Formula 1.99, wherein $R_{20}$ is $C_{3-7}$cycloalkyl;

1.103 Formula I or any of 1.1-1.102, wherein $R_{21}$ is $C_{1-6}$alkyl (e.g., methyl) or —N($R_{18}$)($R_{19}$) and $R_{18}$ and $R_{19}$ are independently H or $C_{1-4}$alkyl;

1.104 Formula 1.103, wherein $R_{21}$ is $C_{1-6}$alkyl (e.g., methyl);

1.105 Formula 1.103, wherein $R_{21}$ is —N($R_{18}$)($R_{19}$) and $R_{18}$ and $R_{19}$ are independently H or $C_{1-4}$alkyl;

1.106 Formula I or any of 1.1-1.105, wherein $R_{22}$ and $R_{23}$ are independently H or $C_{1-4}$alkyl (e.g., methyl);

1.107 Formula 1.106, wherein $R_{22}$ and $R_{23}$ are H, 1.108 Formula 1.106, wherein $R_{22}$ and $R_{23}$ are $C_{1-4}$alkyl (e.g., methyl);

1.109 Formula 1.106, wherein $R_{22}$ is H and $R_{23}$ is $C_{1-4}$alkyl (e.g., methyl);

1.110 any of the preceding formulae wherein the compound is selected from a group consisting of:

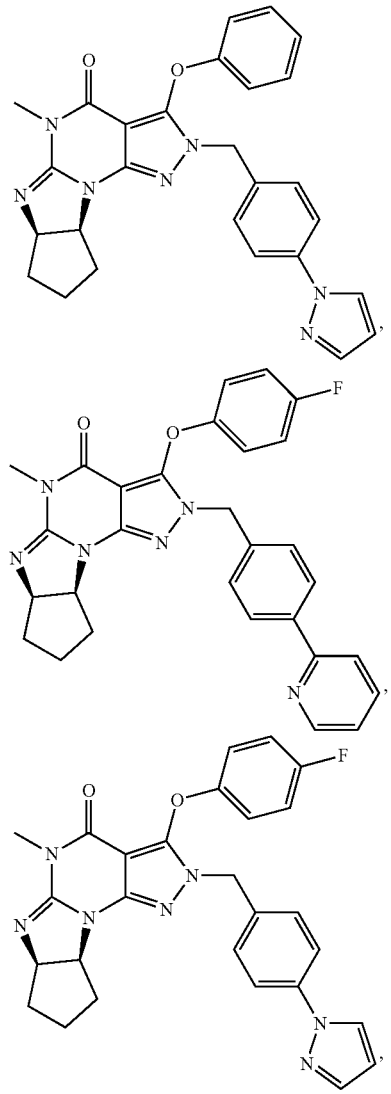

-continued
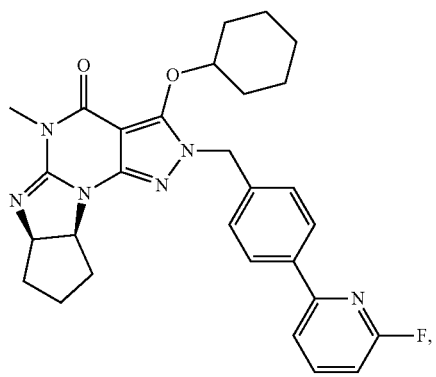
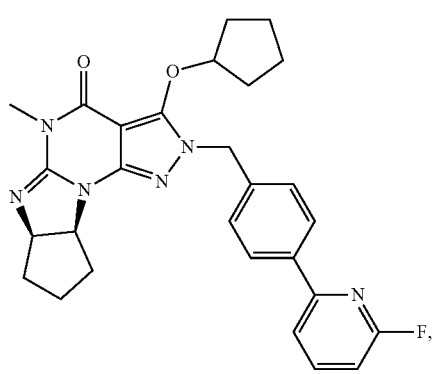
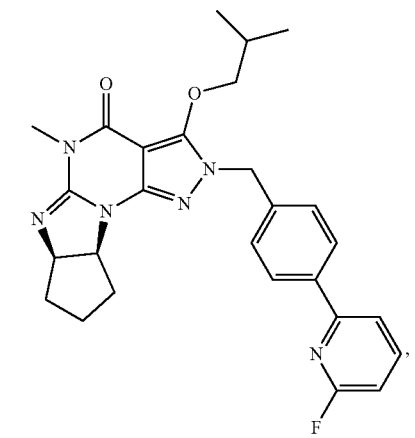
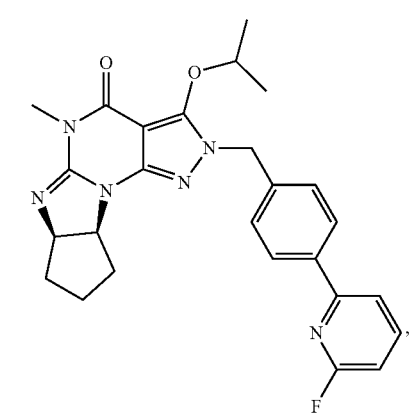
-continued
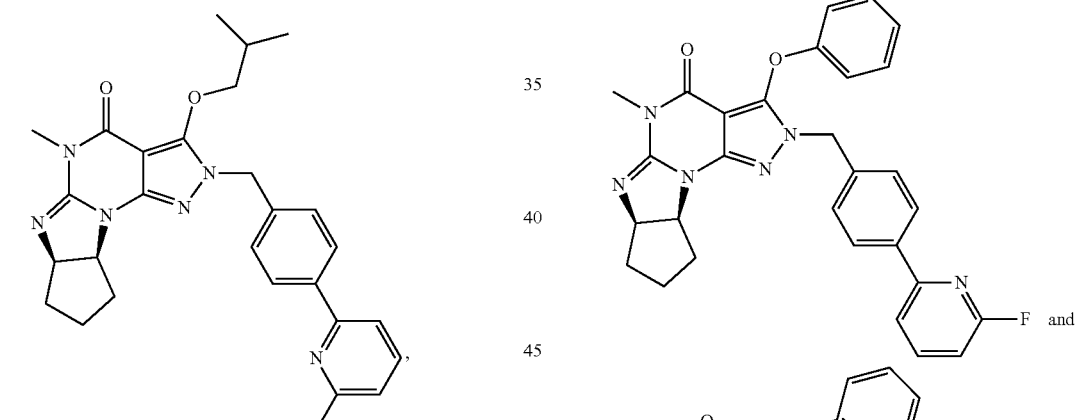
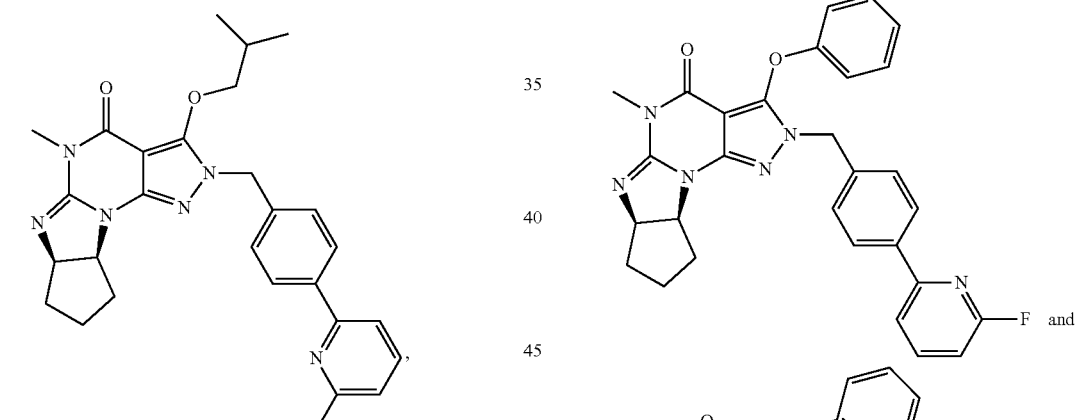
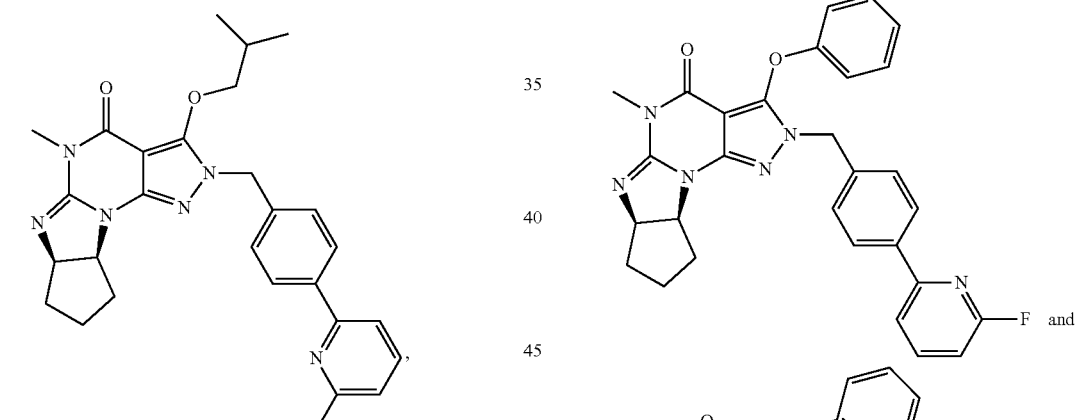
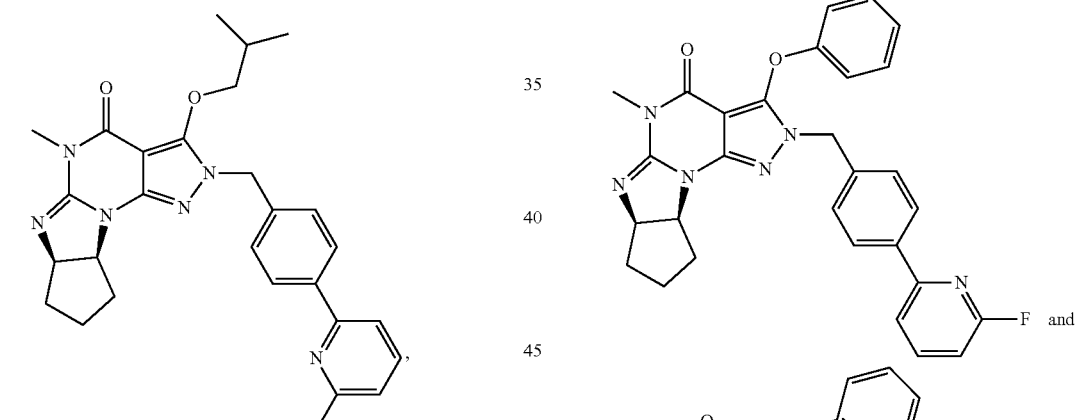 and
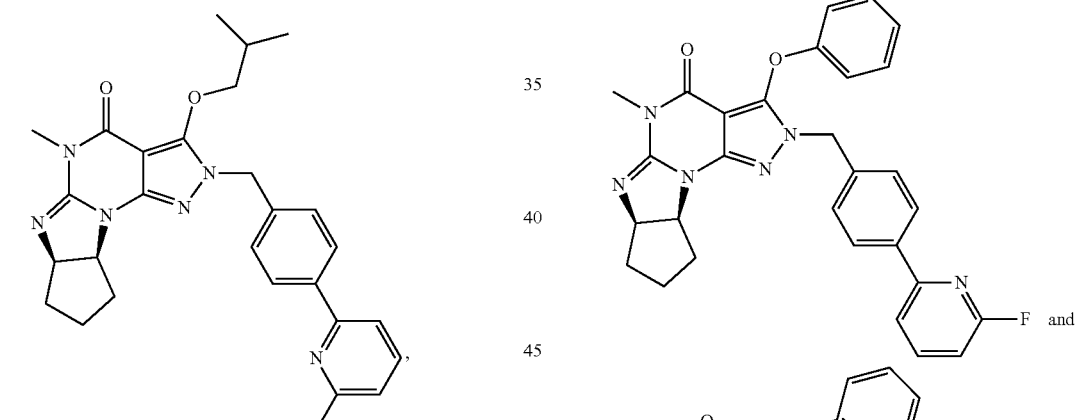
1.111 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 µM, preferably less than 500 nM, more preferably less than 50 nM, still more preferably less than 10 nM, most preferably less than 1 nM in an immobilized-metal affinity particle reagent PDE assay, for example, as described in Example 12, in free or salt form.

In one embodiment, the compound of formula I as described above, is a compound of Formula II:

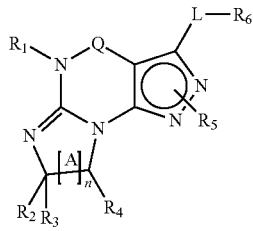

Formula II wherein
(i) Q is —C(=S)—, —C(=N($R_{20}$))—, —C(=O)— or $CH_2$;
(ii) L is a —O—;
(iii) $R_1$ is H or $C_{1-4}$alkyl (e.g., methyl or ethyl);
(iv) $R_4$ is H or $C_{1-4}$alkyl (e.g., methyl or isopropyl) and $R_2$ and $R_3$ are, independently:
H,
$C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
aryl,
heteroaryl,
(optionally hetero)aryl$C_{1-6}$alkoxy, or
(optionally hetero)aryl$C_{1-6}$alkyl, or
$R_2$ and $R_3$ together with the carbon to which they are attached form a 3- to 6-membered ring; or
$R_2$ is H and $R_3$ and $R_4$ together form a di-, tri- or tetramethylene bridge
(pref. wherein the $R_3$ and $R_4$ together have the cis configuration, e.g., where the carbons carrying $R_3$ and $R_4$ have the R and S configurations, respectively);
(v) $R_5$ is
a) -D-E-F, wherein
D is $C_{1-4}$alkylene (e.g., methylene, ethylene or prop-2-yn-1-ylene);
E is arylene (e.g., phenylene); and
F is aryl (e.g., phenyl), heteroaryl (e.g., pyridyl, diazolyl, triazolyl, for example, pyrid-2-yl, imidazol-1-yl, pyrazol-1-yl, 1,2,4-triazol-1-yl), $C_{3-7}$cycloalkyl (e.g., cyclopentyl or cyclohexyl), or hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl), wherein F is optionally substituted with one or more halo or $C_{1-6}$alkyl (e.g., F is 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl, 4-fluorophenyl, 1-methylpyrrolidin-3-yl, 1-methylpyrrolidin-2-yl, 1-ethylpiperidin-1-yl or 1-methylpiperidin-2-yl);
or
b) attached to one of the nitrogen atoms on the pyrazolo portion of Formula II and is a moiety of Formula A

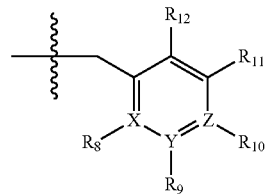

Formula A wherein X, Y and Z are, independently, N or C, and $R_8$, $R_9$, $R_{11}$ and $R_{12}$ are independently H, halogen (e.g., Cl or F), and $R_{10}$ is $C_{3-7}$cycloalkyl, het$C_{3-7}$cycloalkyl (e.g., pyrrolidinyl or piperidinyl, for example piperidin-2-yl or pyrrolidin-2-yl), aryl (e.g., phenyl), or heteroaryl (e.g., pyridyl (for example pyrid-2-yl, pyrid-3-yl, pyrid-4-yl), or thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl or oxadiazolyl (e.g., 1,2,4-oxodiazol-3-yl), wherein the aryl, heteroaryl, cycloalkyl and heterocycloalkyl are independently and optionally substituted with one or more halo (e.g., F or Cl) or $C_{1-4}$alkyl, for example $R_{10}$ is 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl, 4-fluorophenyl, 1-methylpyrrolidin-3-yl, 1-methylpyrrolidin-2-yl, 1-ethylpiperidin-1-yl or 1-methylpiperidin-2-yl;
(vi) $R_6$ is
$C_{1-4}$alkyl (e.g., isopropyl or isobutyl),
$C_{3-7}$cycloalkyl (e.g., cyclopentyl or cyclohexyl),
aryl (e.g., phenyl),
heteroaryl (e.g., pyridyl, for example, pyrid-4-yl),
aryl$C_{1-4}$alkyl (e.g., benzyl),
wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is isopropyl, isobutyl, cyclopentyl, cyclohexyl, phenyl, 3-chlorophenyl or 4-fluorophenyl;
(vii) n=0 or 1;
(viii) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{13}$ or $R_{14}$ can form a di-, tri- or tetramethylene bridge with $R_2$ or $R_4$;
(ix) $R_{20}$ is H, $C_{1-4}$alkyl (e.g., methyl) or $C_{3-7}$cycloalkyl, in free or salt form.

In still another embodiment, the Compound of Formula I as described above is a Compound of Formula III:

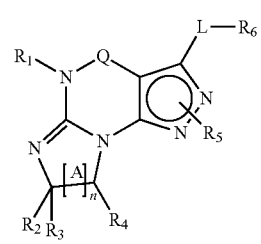

Formula III wherein
(i) Q is —C(=S)—, —C(=N($R_{20}$))—, —C(=O)— or $CH_2$;
(ii) L is a —O—;
(iii) $R_1$ is H or $C_{1-4}$alkyl (e.g., methyl or ethyl);
(iv) $R_4$ is H or $C_{1-4}$alkyl (e.g., methyl, isopropyl) and $R_2$ and $R_3$ are, independently:
H,
$C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
aryl,
heteroaryl,
(optionally hetero)aryl$C_{1-6}$alkoxy,
(optionally hetero)aryl$C_{1-6}$alkyl, or
$R_2$ and $R_3$ together with the carbon to which they are attached form a 3- to 6-membered ring; or
$R_2$ is H and $R_3$ and $R_4$ together form a di-, tri- or tetramethylene bridge
(pref. wherein the $R_3$ and $R_4$ together have the cis configuration, e.g., where the carbons carrying $R_3$ and $R_4$ have the R and S configurations, respectively);
(v) $R_5$ is
a) -D-E-F, wherein
D is $C_{1-4}$alkylene (e.g., methylene, ethylene or prop-2-yn-1-ylene);
E is arylene (e.g., phenylene); and
F is aryl (e.g., phenyl), heteroaryl (e.g., pyridyl, diazolyl, triazolyl, for example, pyrid-2-yl, imidazol-1-yl, pyrazol-1-yl, 1,2,4-triazol-1-yl), $C_{3-7}$cycloalkyl (e.g., cyclopentyl or cyclohexyl), or hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl), wherein F is optionally substituted with one or more halo or $C_{1-6}$alkyl (e.g., F is 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl, 4-fluorophenyl, 1-methylpyrrolidin-3-yl, 1-methylpyrrolidin-2-yl, 1-ethylpiperidin-1-yl or 1-methylpiperidin-2-yl);
or
b) attached to one of the nitrogen atoms on the pyrazolo portion of Formula III and is a moiety of Formula A

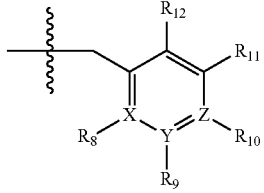

Formula A wherein X, Y and Z are, independently, N or C, and $R_8$, $R_9$, $R_{11}$ and $R_{12}$ are independently H or halogen (e.g., Cl or F), and $R_{10}$ is $C_{3-7}$cycloalkyl, het$C_{3-7}$cycloalkyl (e.g., pyrrolidinyl or piperidinyl, for example piperidin-2-yl or pyrrolidin-2-yl), aryl (e.g., phenyl), or heteroaryl (e.g., pyridyl (for example pyrid-2-yl, pyrid-3-yl, pyrid-4-yl), or thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl, oxadiazolyl (e.g., 1,2,4-oxodiazol-3-yl), wherein the aryl, heteroaryl, cycloalkyl and heterocycloalkyl are independently and optionally substituted with one or more halo (e.g., F or Cl) or $C_{1-4}$alkyl;

(vi) $R_6$ is:
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl),
wherein the aryl or heteroaryl is optionally substituted with one or more halo (e.g., F or Cl), hydroxy or $C_{1-6}$alkyl, for example, $R_6$ is 3-chlorophenyl or 4-fluorophenyl, (vii) n=0 or 1;

(viii) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{13}$ or $R_{14}$ can form a di-, tri- or tetramethylene bridge with $R_2$ or $R_4$;

(x) $R_{20}$ is H, $C_{1-4}$alkyl (e.g., methyl) or $C_{3-7}$cycloalkyl,
in free or salt form.

In still another embodiment of the invention, the Compound of Formula I is a compound of Formula IV:

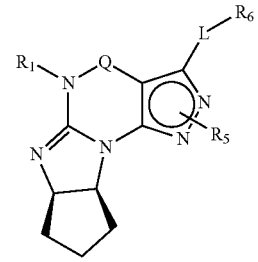

Formula IV wherein:
(i) Q is —C(=S)—, —C(=N($R_{20}$))—, —C(=O)— or $CH_2$;
(ii) L is a —O—;
(iii) $R_1$ is H or $C_{1-4}$alkyl (e.g., methyl or ethyl);
(iv) $R_5$ is
a) -D-E-F, wherein
D is $C_{1-4}$alkylene (e.g., methylene, ethylene or prop-2-yn-1-ylene);
E is arylene (e.g., phenylene);
F is aryl (e.g., phenyl), heteroaryl (e.g., pyridyl, diazolyl, triazolyl, for example, pyrid-2-yl, imidazol-1-yl, pyrazol-1-yl, 1,2,4-triazol-1-yl), $C_{3-7}$cycloalkyl (e.g., cyclopentyl or cyclohexyl), or hetero$C_{3-7}$cycloalkyl (e.g., pyrrolidinyl (for example, pyrrolidin-1-yl, pyrrolidin-2-yl or pyrrolidin-3-yl), piperidinyl (e.g., piperidin-2-yl), tetrahydro-2H-pyran-4-yl or morpholinyl), wherein F is optionally substituted with one or more halo or $C_{1-6}$alkyl (e.g., F is 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl, 4-fluorophenyl, 1-methylpyrrolidin-3-yl, 1-methylpyrrolidin-2-yl, 1-ethylpiperidin-1-yl or 1-methylpiperidin-2-yl);

or b) attached to one of the nitrogen atoms on the pyrazolo portion of Formula IV and is a moiety of Formula A

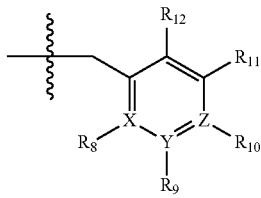

Formula A wherein X, Y and Z are, independently, N or C, and $R_8$, $R_9$, $R_{11}$ and $R_{12}$ are independently H or halogen (e.g., Cl or F), and $R_{10}$ is $C_{3-7}$cycloalkyl, het$C_{3-7}$cycloalkyl (e.g., pyrrolidinyl or piperidinyl, for example piperidin-2-yl or pyrrolidin-2-yl), aryl (e.g., phenyl), or heteroaryl (e.g., pyridyl (for example pyrid-2-yl, pyrid-3-yl, pyrid-4-yl), or thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl, oxadiazolyl (e.g., 1,2,4-oxodiazol-3-yl), wherein the aryl, heteroaryl, cycloalkyl and heterocycloalkyl are independently and optionally substituted with one or more halo (e.g., F or Cl), $C_{1-4}$alkyl;

(v) $R_6$ is:
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl),
wherein the aryl or heteroaryl is optionally substituted with one or more halo (e.g., F, Cl), hydroxy or $C_{1-6}$alkyl, for example, $R_6$ is 3-chlorophenyl or 4-fluorophenyl, (xi) $R_{20}$ is H, $C_{1-4}$alkyl (e.g., methyl) or $C_{3-7}$cycloalkyl, in free or salt form.

In yet another embodiment, the Compound of Formula I is a compound of Formula V:

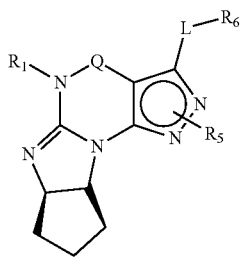

Formula V wherein:
(i) Q is —C(=O)—;
(ii) L is —O—;
(iii) $R_1$ is $C_{1-4}$alkyl (e.g., methyl or ethyl);
(iv) $R_5$ is attached to one of the nitrogen atoms on the pyrazolo portion of Formula V and is a moiety of Formula A

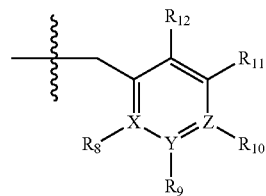

Formula A wherein X, Y and Z are C, and $R_8$, $R_9$, $R_{11}$ and $R_{12}$ are independently H, and $R_{10}$ is:
het$C_{3-7}$cycloalkyl (e.g., pyrrolidinyl or piperidinyl, for example piperidin-2-yl or pyrrolidin-2-yl),
aryl (e.g., phenyl), or
heteroaryl (e.g., pyridyl (for example pyrid-2-yl, pyrid-3-yl, pyrid-4-yl), or thiadiazolyl (e.g., 1,2,3-thiadiazol-4-yl)), diazolyl (e.g., imidazol-1-yl or pyrazol-1-yl), triazolyl (e.g., 1,2,4-triazol-1-yl), tetrazolyl or oxadiazolyl (e.g., 1,2,4-oxodiazol-3-yl),
wherein the aryl, heteroaryl, cycloalkyl and heterocycloalkyl are independently and optionally substituted with one or more halo (e.g., F or Cl), $C_{1-4}$alkyl, for example $R_{10}$ is 4-methyl-imidazol-1-yl, 1-methyl-imidazol-2-yl, 5-fluoropyrid-2-yl, 6-fluoropyrid-2-yl, 3-fluoropyrid-2-yl, 4-fluoropyrid-2-yl, 4,6-dichloropyrid-2-yl, 4-fluorophenyl, 1-methylpyrrolidin-3-yl, 1-methylpyrrolidin-2-yl, 1-ethylpiperidin-1-yl or 1-methylpiperidin-2-yl;

(v) $R_6$ is
$C_{3-7}$cycloalkyl (e.g., cyclopentyl or cyclohexyl),
aryl (e.g., phenyl),
heteroaryl (e.g., pyridyl, for example, pyrid-4-yl),
aryl$C_{1-4}$alkyl (e.g., benzyl),
wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is isopropyl, isobutyl, cyclopentyl, cyclohexyl, phenyl, 3-chlorophenyl or 4-fluorophenyl,
in free or salt form.

In another embodiment, the Compound of Formula I is a compound of Formula VI:

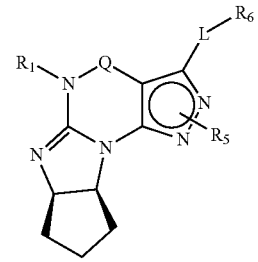

Formula VI wherein:
(i) Q is —C(=O)—;
(ii) L is —O—;
(iii) $R_1$ is $C_{1-4}$alkyl (e.g., methyl or ethyl);
(iv) $R_5$ is attached to one of the nitrogen atoms on the pyrazolo portion of Formula VI and is a moiety of Formula A

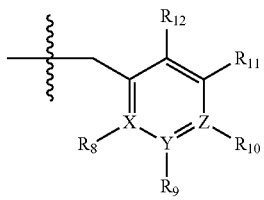

Formula A wherein X, Y and Z are C, and $R_8$, $R_9$, $R_{11}$ and $R_{12}$ are independently H, and $R_{10}$ is selected from piperidinyl (e.g., piperidin-2-yl), pyrrolidinyl (e.g., pyrrolidin-2-yl), pyridyl (for example pyrid-2-yl, pyrid-3-yl), diazolyl (e.g., pyrazol-1-yl), 6-fluoropyrid-2-yl, 1-methylpyrrolidin-3-yl, 1-methylpyrrolidin-2-yl, 1-ethylpiperidin-1-yl or 1-methylpiperidin-2-yl;

(v) $R_6$ is $C_{3-7}$cycloalkyl (e.g., cyclopentyl or cyclohexyl), aryl (e.g., phenyl), heteroaryl (e.g., pyridyl, for example, pyrid-4-yl), aryl$C_{1-4}$alkyl (e.g., benzyl), wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is cyclopentyl, cyclohexyl, phenyl, 3-chlorophenyl or 4-fluorophenyl, in free or salt form.

In still another embodiment, the invention provides a Compound of Formula VII:

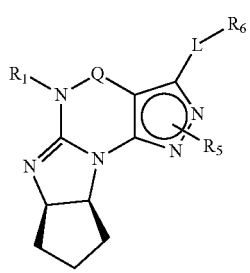

Formula VII wherein:
(i) Q is —C(=O)—;
(ii) L is —O—;
(iii) $R_1$ is $C_{1-4}$alkyl (e.g., methyl or ethyl);
(iv) $R_5$ is attached to one of the nitrogen atoms on the pyrazolo portion of Formula VII and is a moiety of Formula A

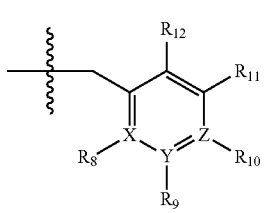

Formula A wherein X, Y and Z are C, and $R_8$, $R_9$, $R_{11}$ and $R_{12}$ are independently H, and $R_{10}$ is selected from piperidinyl (e.g., piperidin-2-yl), pyrrolidinyl (e.g., pyrrolidin-2-yl), pyridyl (for example pyrid-2-yl, pyrid-3-yl), diazolyl (e.g., pyrazol-1-yl), 6-fluoropyrid-2-yl, 1-methylpyrrolidin-3-yl, 1-methylpyrrolidin-2-yl, 1-ethylpiperidin-1-yl or 1-methylpiperidin-2-yl;

(v) $R_6$ is selected from cyclopentyl, cyclohexyl, phenyl, 3-chlorophenyl or 4-fluorophenyl, in free or salt form.

In still another embodiment, the invention provides a Compound of Formula VIII:

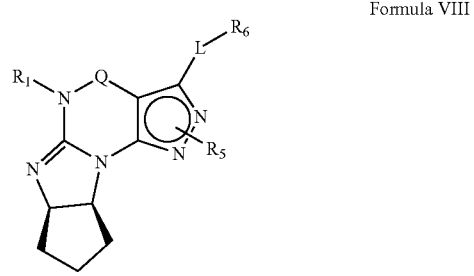

Formula VIII wherein:
(i) Q is —C(=O)—;
(ii) L is —O—;
(iii) $R_1$ is $C_{1-4}$alkyl (e.g., methyl or ethyl);
(iv) $R_5$ is attached to one of the nitrogen atoms on the pyrazolo portion of Formula VIII and is a moiety of Formula A

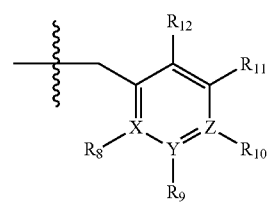

Formula A wherein X, Y and Z are C, and $R_8$, $R_9$, $R_{11}$ and $R_{12}$ are independently H, and $R_{10}$ is pyrid-2-yl, 6-fluoropyrid-2-yl, 1-methylpyrrolidin-3-yl, 1-methylpyrrolidin-2-yl, 1-ethylpiperidin-1-yl or 1-methylpiperidin-2-yl;

(v) $R_6$ is phenyl or 4-fluorophenyl, in free or salt form.

In still another embodiment, the invention provides a compound of any of the foregoing formulae, e.g., any of Formula I-VIII or any of formulae 1.1-1.111, wherein $R_{10}$ is selected from any of 3-fluoropyrid-2-yl and 4-fluoropyrid-2-yl, 5-fluoropyrid-2-yl, 6-fluoropyrid-2-yl.

If not otherwise specified or clear from context or unless otherwise specified, the following terms herein have the following meanings:

(a) "Alkyl" as used herein is a saturated or unsaturated hydrocarbon moiety, preferably saturated, preferably having one to six carbon atoms, in some instances one to four carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, comprising three to nine carbon atoms, in some instances three to seven atoms, at least some of which form a nonaromatic mono- or bicyclic, or bridged cyclic structure, and which may be optionally substituted, e.g., with halogen (e.g., chloro or fluoro), hydroxy or carboxy.

(c) "Heterocycloalkyl" is, unless otherwise indicated, saturated or unsaturated nonaromatic hydrocarbon moiety, preferably saturated, comprising three to nine carbon atoms, in some instances three to seven atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy or carboxy.

(d) "Aryl" as used herein is a mono or bicyclic aromatic hydrocarbon, preferably phenyl. In some instances, aryl is optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur, oxygen or nitrogen rather than carbon, e.g., pyridyl or thiadiazolyl which may be optionally substituted, e.g., with alkyl, halogen, haloalkyl, hydroxy or carboxy.

(f) Wherein E is phenylene, the numbering is as follows:

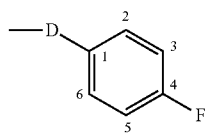

(g) It is intended that wherein the substituents end in "ene", for example, alkylene, phenylene or arylalkylene, said substituents are intended to bridge or be connected to two other substituents. Therefore, methylene is intended to be —$CH_2$—, ethylene is intended to be —$CH_2$—$CH_2$— and phenylene intended to be —$C_6H_4$— and arylalkylene is intended to be —$C_6H_4$—$CH_2$— or —$CH_2$—$C_6H_4$—.

(h) The Compounds of the Invention are intended to be numbered as follows:

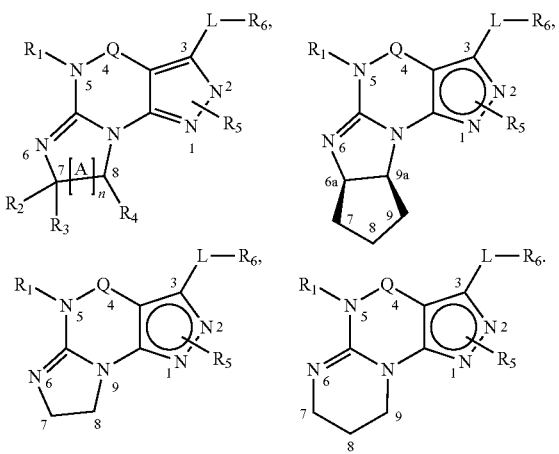

The term "substituted," as used herein, means that any one or more hydrogens on the designated atom is replaced with a selection from the indicated group, provided that the designated atom's normal valency is not exceeded, and that the substitution results in a stable compound. Similarly, the substituents defined for the Compounds of the Invention are intended to result in stable compounds.

Compounds of the Invention, encompassing any of the compounds disclosed herein, e.g., optionally substituted 4,5,7,8-tetrahydro-(optionally 4-oxo, 4-thioxo or 4-imino)-(1H or 2H)-imidazo[1,2-a]pyrazolo[4,3-e]pyrimidine or 4,5,7,8,9-pentahydro-(1H or 2H)-(optionally 4-oxo, 4-thioxo or 4-imino)-pyrimido[1,2-a]pyrazolo[4,3-e]pyrimidine compounds, e.g., (1 or 2 and/or 3 and/or 5)-substituted: 4,5,7,8-tetrahydro-(1H or 2H)-imidazo[1,2-a]pyrazolo[4,3-e]pyrimidine, 4,5,7,8-tetrahydro-(1H or 2H)-imidazo[1,2-a]pyrazolo[4,3-e]pyrimidine-4(5H)-one, 4,5,7,8-tetrahydro-(1H or 2H)-imidazo[1,2-a]pyrazolo[4,3-e]pyrimidine-4(5H)-thione, 4,5,7,8-tetrahydro-(1H or 2H)-imidazo[1,2-a]pyrazolo[4,3-e]pyrimidine-4(5H)-imine, 4,5,7,8,9-pentahydro-(1H or 2H)-pyrimido[1,2-a]pyrazolo[4,3-e]pyrimidine, 4,5,7,8,9-pentahydro-(1H or 2H)-pyrimido[1,2-a]pyrazolo[4,3-e]pyrimidine-4(5H)-one, 4,5,7,8,9-pentahydro-(1H or 2H)-pyrimido[1,2-a]pyrazolo[4,3-e]pyrimidine-4(5H)-thione, 4,5,7,8,9-pentahydro-(1H or 2H)-pyrimido[1,2-a]pyrazolo[4,3-e]pyrimidine-4(5H)-imine compounds, e.g., Compounds of Formula I, e.g., any of formulae 1.1-1.111, or Compounds of any of Formulae II-VIII as described herein, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. In particular embodiment, the salt of the compounds of the invention is a formic acid addition salt.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, for example, Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, for example, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

The invention also provides methods of making the Compounds of the Invention and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, cognitive impairment of schizophrenia, narcolepsy and diseases that may be alleviated by the enhancement of progesterone-signaling such as female sexual dysfunction), or a disease or disorder such as psychosis or glaucoma). This list is not intended to be exhaustive and may include other diseases and disorders as set forth below.

In another embodiment, the invention further provides a pharmaceutical composition comprising a Compound of the Invention, in free or pharmaceutically acceptable salt form, in admixture with a pharmaceutically acceptable carrier.

DETAILED DESCRIPTION OF THE INVENTION

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. Various starting materials and/or Compounds of the Invention may be prepared using methods described in WO 2006/133261; WO 2009/075784; PCT/US2009/06438 (or WO 2010/065148); PCT/US2009/006442 (or WO 2010/065151) and PCT/US2009/006439 (or WO 2010/065149). All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

As will be appreciated by those skilled in the art, the Compounds of the Invention may exhibit keto-enol tautomerization. Therefore, the invention as defined in the present invention is to be understood as embracing both the structures as set forth herewith and their tautomeric forms.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{23}I$, $^{131}I$, $^{125}I$, $^{11}C$, $^{18}F$, may replace the corresponding abundant species, e.g., I, C and F respectively. Another example of useful isotope of the compound of the invention is the $^{11}C$ isotope. These radio isotopes are useful for radio-imaging and/or pharmacokinetic studies of the compounds of the invention. Methods of making isotopes of PDE1 inhibitors disclosed in WO 2011/043816, the contents of which are incorporated by reference in their entirety, may be used for making the isotopes of the compounds of the current invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations:
BOP=(Benzotriazole-1-yl-oxy)tris(dimethylamino)-phosphonium hexafluorophosphate,
BuLi=n-butyllithium,
Bu$^t$OH=tert-butyl alcohol,
CAN=ammonium cerium (IV) nitrate,
DBU=1,8-Diazabicyclo[5.4.0]undec-7-ene,
DIPEA=diisopropylethylamine,
DMF=N,N-dimethylformamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
K$_2$CO$_3$=potassium carbonate
LiHMDS=lithium bis(trimethylsilyl)amide
LDA=lithium diisopropylamide
MeOH=methanol,
NBS=N-bromosuccinimide,
NCS=N-chlorosuccinimide,
NaHCO$_3$=sodium bicarbonate,
NH$_4$OH=ammonium hydroxide,
Pd$_2$ (dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid
THF=tetrahydrofuran.

The synthetic methods in this invention are illustrated below. The significances for the R groups are as set forth above for formula I-VIII or any of formulae 1.1-1.111 unless otherwise indicated.

In an aspect of the invention, intermediate compounds of formula IIb can be synthesized by reacting a compound of formula IIa with a dicarboxylic acid, acetic anhydride and acetic acid mixing with heat, e.g., to about 90° C. for about 3 hours and then cooled:

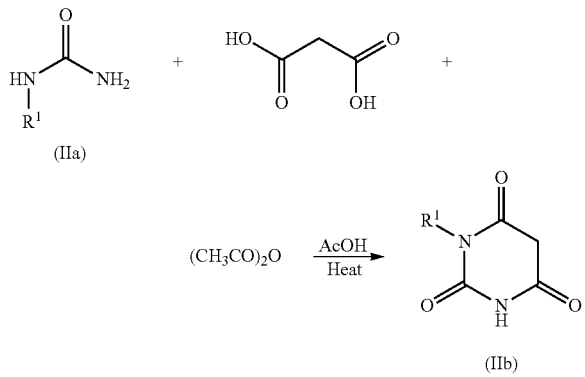

wherein R¹ is methyl.

Intermediate IIc can be prepared by for example reacting intermediate IIb with for example a chlorinating compound such as POCl₃, sometimes with small amounts of water and heat, e.g., heating to about 80° C. for about 4 hours and then cooled:

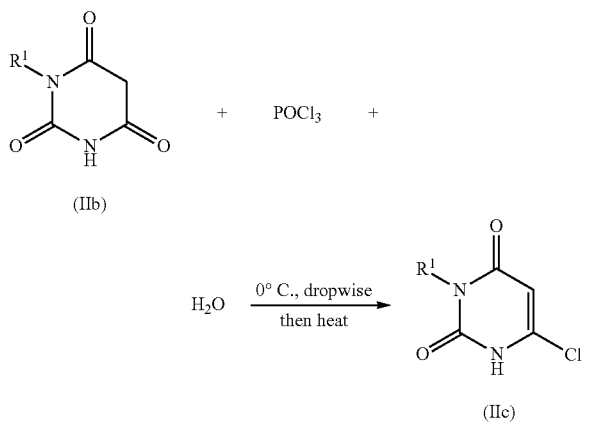

Intermediate IId may be formed by reacting intermediate IIc with for example a P¹-L in a solvent such as DMF and a base such as K₂CO₃, sodium bicarbonate, cesium carbonate, sodium hydroxide, triethylamine, diisopropylethylamine or the like at room temperature or with heating:

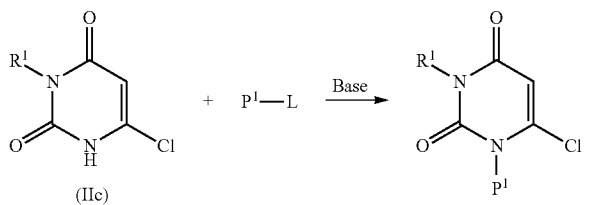

wherein P¹ is a protective group [e.g., p-methoxybenzyl group (PMB) or BOC]; L is a leaving group such as a halogen, mesylate, or tosylate. Preferably, P¹ is PMB and the base is potassium carbonate.

Intermediate IIe may be prepared by reacting intermediate IId with hydrazine or hydrazine hydrate in a solvent such as methanol and with heating, e.g. refluxed for about 4 hours and then cooled:

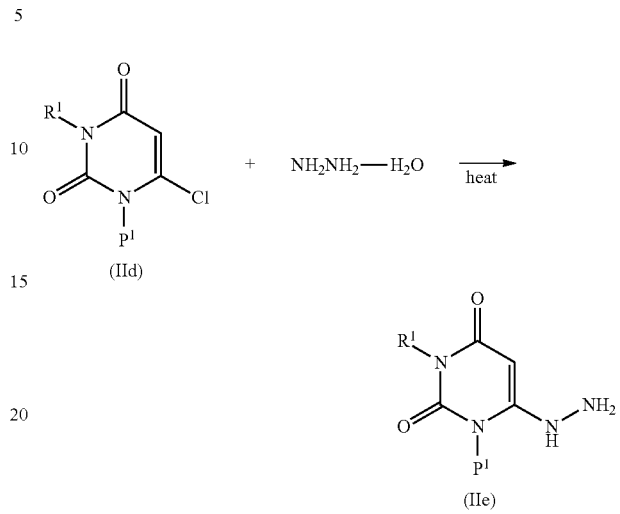

Intermediate IVa may be formed by for example reacting intermediate IIe with POCl₃ and DMF:

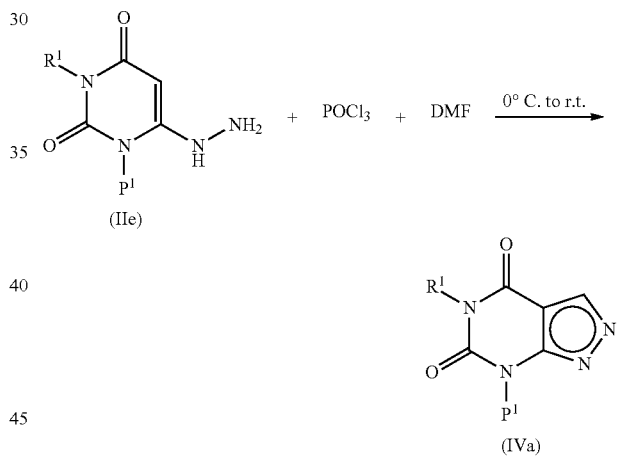

wherein R¹ is as defined previously, such as a methyl group.

Intermediate IVb may be formed by reacting intermediate IVa with for example a R₅—X in a solvent such as DMF and a base such as K₂CO₃, sodium bicarbonate, cesium carbonate, triethylamine or the like at room temperature or with heating (Reaction 1):

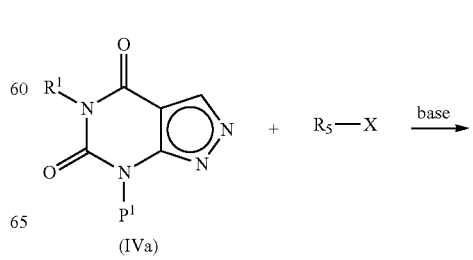

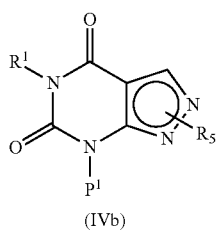

(IVb)

Intermediate IVc may be synthesized from intermediate IVb by removing the protective group P¹ with an appropriate method. For example, if P¹ is a PMB group, then it can be removed with CAN or TFA/TFMSA at room temperature (Reaction 2):

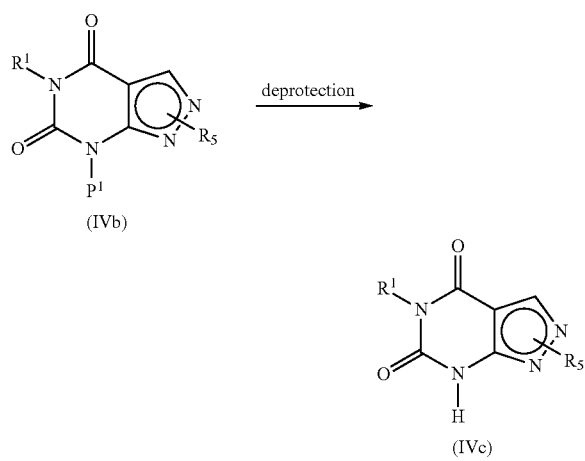

Wherein P¹ is BOC, the compound may be deprotected by using acid such as hydrochloric acid or TFA.

Intermediate IVd can be prepared by reacting intermediate IVc with for example a chlorinating compound such as POCl₃ and optionally with heating, e.g., reflux for about 2 days, or heated at 150~200° C. for about 5-10 min in a sealed vial with a microwave instrument and then cooled (Reaction 3):

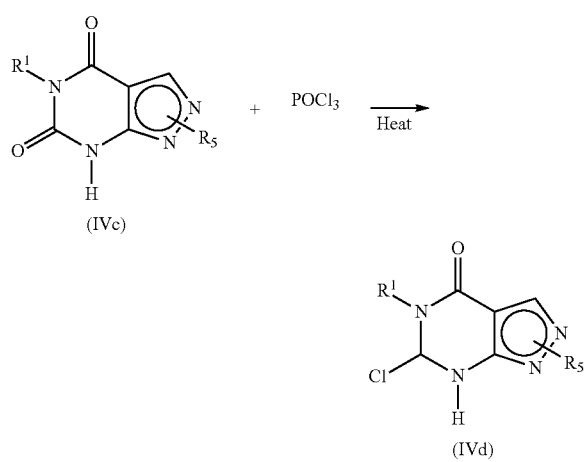

Intermediate IVe can be formed by reacting a intermediate IVd with an amino alcohol under basic condition in a solvent such as DMF and heated overnight then cooled (Reaction 4A):

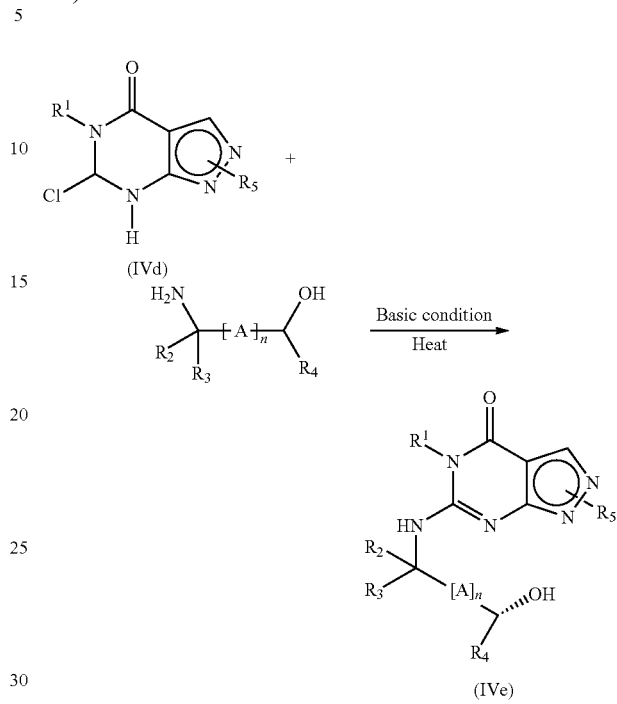

Alternatively, intermediate IVe can be synthesized directly from intermediate IVc by reacting with an amino alcohol and a coupling reagent such as BOP in the presence of a base such as DBU (Reaction 4B):

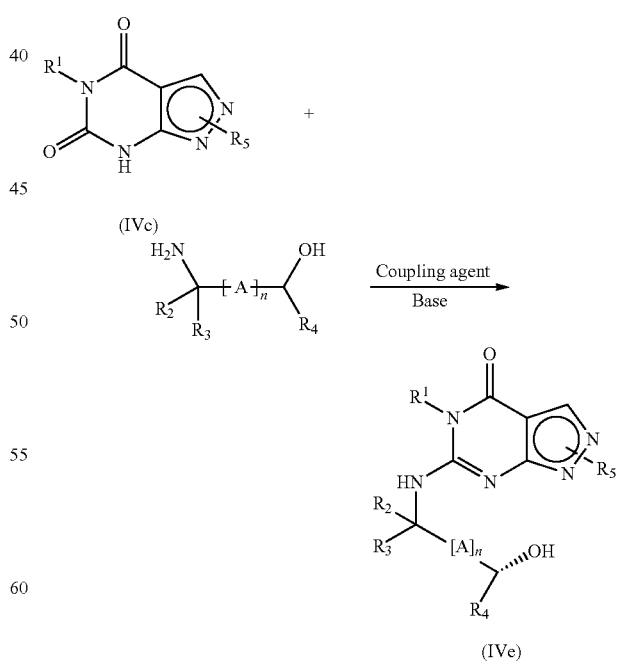

wherein all the substituents are as defined previously.

Intermediate IVf may be formed by reacting a compound of IVe with for example a dehydrating/halogenating agent such as SOCl$_2$ in a solvent such as CH$_2$Cl$_2$ at room temperature overnight or heated at 35° C. for several hours, and then cooled (Reaction 5):

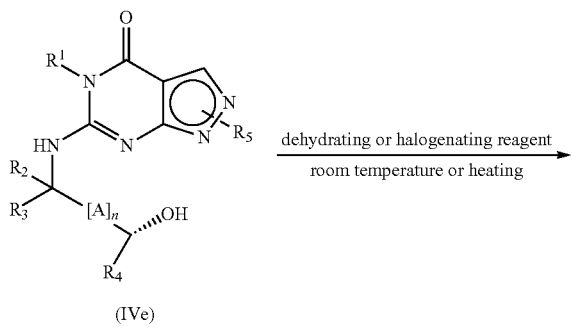

(IVe)

dehydrating or halogenating reagent
room temperature or heating
→

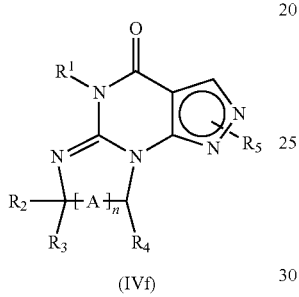

(IVf)

Intermediate IVg wherein X is halogen (e.g., chloro) may be formed by reacting intermediate IVf with for example a halogenating agent such as hexachloroethane, NCS, NBS, I$_2$ and a base such as LiHMDS in a solvent such as THF at low temperature for several hours (Reaction 6).

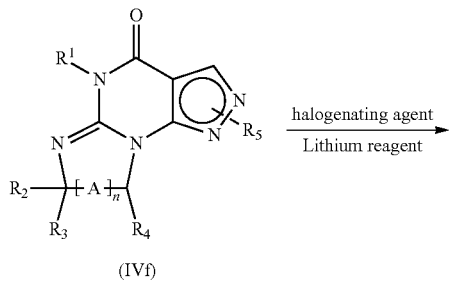

(IVf)

halogenating agent
Lithium reagent
→

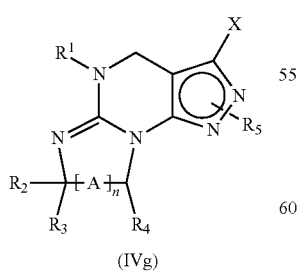

(IVg)

The Compounds of the Invention may be formed by reacting intermediate IVg wherein X is halogen (e.g., chloro) with R$_6$—OH with heating (Reaction 7):

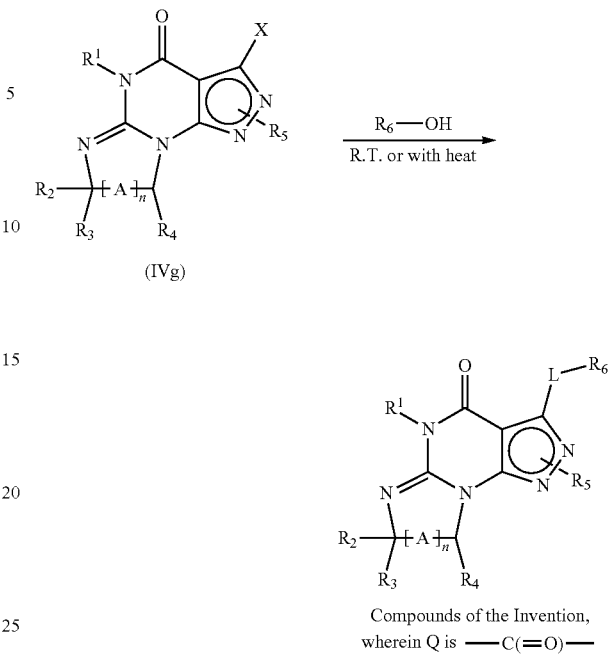

The Compounds of the Invention wherein Q is CH$_2$ may be prepared by reacting the Compounds of the Invention wherein Q is C(═O) with a reducing agent, e.g., DIBAL-H or LAH, preferably DIBAL-H.

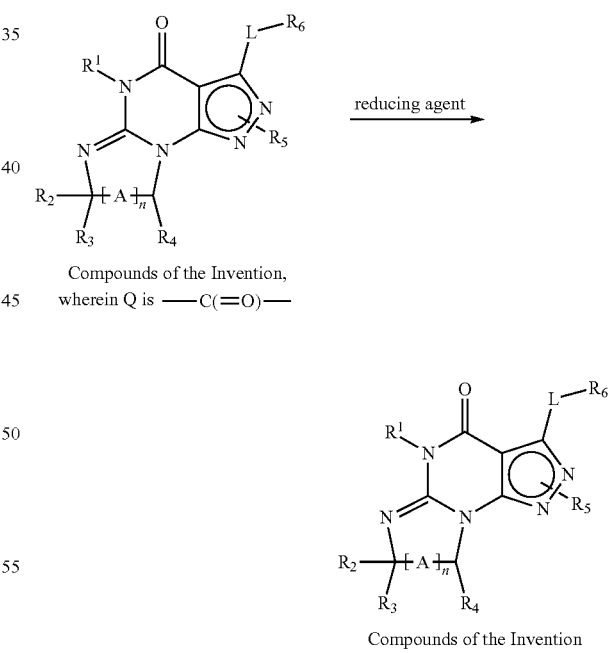

The Compounds of the Invention wherein Q is C(═S) may be prepared by reacting Compounds of the Invention wherein Q is C(═O) with P$_4$S$_{10}$ with P$_4$S$_{10}$ in a microwave vial in the presence of a base, e.g., pyridine, and optionally heating the mixture to an elevated temperature, e.g., in a microwave, e.g., to about 150° C.

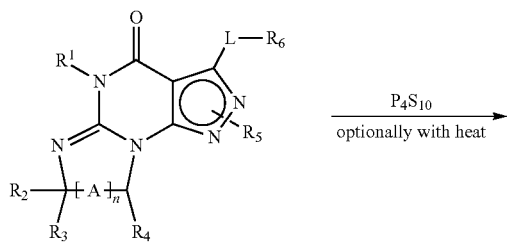

Compounds of the Invention,
wherein Q = C(═O)

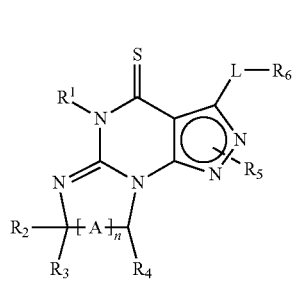

Compounds of the Invention,
wherein Q = C(═S)

Compounds of the Invention wherein Q is C(═N(R$_{20}$)) may be prepared by reacting a compound of the Invention wherein Q is C(═S) with NH$_2$ (R$_{20}$) in the presence of HgCl$_2$ upon heating.

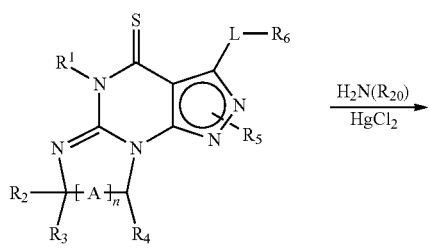

Compounds of the Invention,
wherein Q = C(═S)

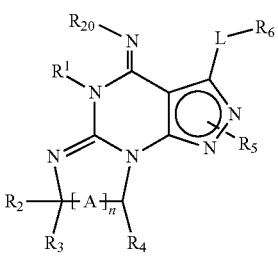

Compounds of the Invention,
wherein Q = C(═N(R$_{20}$))

Alternatively, the invention provides methods of making the Compounds of the Invention, for example, comprising reacting intermediate (I)-A with for example R$_5$—X in a solvent such as DMF and a base such as K$_2$CO$_3$, cesium carbonate,

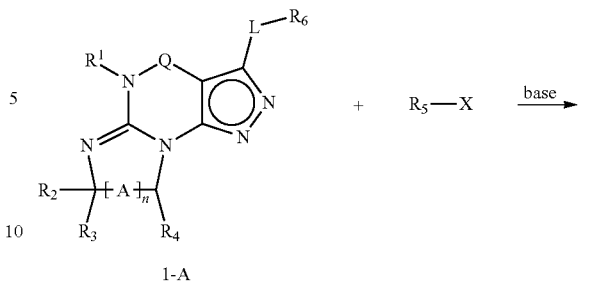

1-A

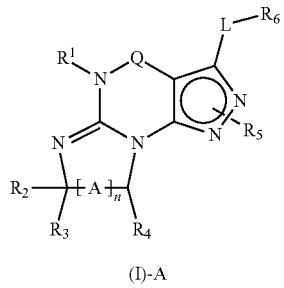

(I)-A wherein all the substitutents are as defined previously in any of Formulae I-VIII; X is a leaving group such as a halogen, mesylate, or tosylate.

Reactions 1-6 referenced above are useful for preparing intermediates useful for the preparation of compounds of similar core structures, e.g., such as compounds described in WO 2006/133261, WO 2009/075784, PCT/US2009/006442 (or WO 2010/065151) and PCT/US2009/006439 (or WO 2010/065149), the contents of each of which are incorporated by reference in their entirety. Therefore, the invention claims all intermediates disclosed herein, particularly compounds or intermediates of formulae (IVa), (IVB), (IVc), (IVd), (IVe), (IVf) and (IVg). Reactions 1-6 referenced above are not only useful methods for preparing Compounds of the current Invention, but are also useful for preparing compounds as disclosed in WO 2006/133261, WO 2009/075784, PCT/US2009/006442 (or WO 2010/065151) and PCT/US2009/006439 (or WO 2010/065149). Therefore the invention provides a method of making a compound as disclosed in WO 2006/133261, WO 2009/075784, PCT/US2009/006442 (or WO 2010/065151) and PCT/US2009/006439 (or WO 2010/065149), comprising the step(s) as described in any of Reactions 1-6 wherein the intermediates are as defined in the respective applications, for example, as defined in WO 2006/133261 or WO 2009/075784. For example, Intermediate (IVc) as defined in WO 2009/075784 is reacted with an amino alcohol and a coupling reagent such as BOP in the presence of a base such as DBU as described in Reaction 4B to form intermediate of formula (IVe) as defined in WO 2009/075784. Similarly, Intermediate (IVc) as defined in WO 2006/133261 may be reacted with an amino alcohol and a coupling reagent such as BOP in the presence of a base such as DBU as described in Reaction 4B to form intermediate of formula (IVe) as defined in WO 2006/133261. Compound Ia as defined in WO 2006/133261 may be reacted with a halogenating agent such as hexachloroethane, NCS, NBS, I$_2$ and a base such as LiHMDS in a solvent such as THF at low temperature for several hours as described in Reaction 6. The resulting product may then be reacted with R$_6$—NH$_2$ wherein R$_6$ is as defined in WO 2006/133261 optionally in the presence of a catalyst such as Pd$_2$(pda)$_3$ and a ligand such as xantphos and a base such as potassium carbonate to yield the compound as defined in WO 2006/133261.

Alternatively, Reactions 1-6 may be performed in different order, e.g., wherein Reaction 6 is performed on intermediate (IVb), e.g., reacting intermediate (IVb) with a halogenating agent such as hexachloroethane, NCS, NBS, $I_2$ and optionally with a base such as LiHMDS in a solvent such as THF at low temperature for several hours. The resulting product may then be reacted with $R_6$—$NH_2$ wherein $R_6$ is as defined in WO 2006/133261 optionally in the presence of a catalyst such as $Pd_2$ $(pda)_3$ and a ligand such as xantphos and a base such as potassium carbonate to yield the compound as defined in WO 2006/133261. The resulting product is then deprotected as described in Reaction 2 above. The deprotected product is reacted with an amino alcohol and a coupling reagent such as BOP in the presence of a base such as DBU as described in Reaction 4B followed by the reaction as described in Reaction 5.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension or pulmonary hypertension, and sexual dysfunction;

(iv) Respiratory and inflammatory disorders, including asthma, chronic obstructive pulmonary disease, and allergic rhinitis, as well as autoimmune and inflammatory diseases;

(v) Any disease or condition characterized by low levels of cAMP and/or cGMP (or inhibition of cAMP and/or cGMP signaling pathways) in cells expressing PDE1; and/or (vi) Any disease or condition characterized by reduced dopamine D1 receptor signaling activity, comprising administering an effective amount of a Compound of the Invention, e.g., any of Formulae I-VIII or 1.1-1.111, in free or pharmaceutically acceptable salt form, to a human or animal patient in need thereof.

In an especially preferred embodiment, the invention provides methods of treatment or prophylaxis for narcolepsy. In this embodiment, PDE 1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of (i) a PDE 1 Inhibitor, e.g., any of Formulae I-VIII or 1.1-1.111, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

in free or pharmaceutically acceptable salt form, to a human or animal patient in need thereof. The Compounds of the Invention may be used as a sole therapeutic agent or use in combination for co-administered with another active agent.

In another embodiment, the invention further provides methods of treatment or prophylaxis of a condition which may be alleviated by the enhancement of the progesterone signaling comprising administering an effective amount of a Compound of the Invention, e.g., any of Formulae I-VIII or 1.1-1.111, in free or pharmaceutically acceptable salt form, to a human or animal patient in need thereof. Disease or condition that may be ameliorated by enhancement of progesterone signaling include, but are not limited to, female sexual dysfunction, secondary amenorrhea (e.g., exercise amenorrhea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of (i) a PDE 1 Inhibitor, e.g., any of Formulae I-VIII or 1.1-1.111, and (ii) a hormone, e.g., selected from estrogen and estrogen analogues (e.g., estradiol, estriol, estradiol esters) and progesterone and progesterone analogues (e.g., progestins)

in free or pharmaceutically acceptable salt form, to a human or animal patient in need thereof.

The invention also provides a method for enhancing or potentiating dopamine D1 intracellular signaling activity in a cell or tissue comprising contacting said cell or tissue with an amount of a Compound of the Invention, e.g., any of Formulae I-VIII or 1.1-1.111, sufficient to inhibit PDE1B activity, e.g., PDE1A or PDE1B activity.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., any of Formulae I-VIII or 1.1-1.111, in that inhibits PDE1B, wherein PDE1B activity modulates phosphorylation of DARPP-32 and/or the GluR1 AMPA receptor.

In another aspect, the invention also provides a method for the treatment for glaucoma or elevated intraocular pressure comprising topical administration of a therapeutically effective amount of a phosphodiesterase type I (PDE1) Inhibitor of the Invention, in free or pharmaceutically acceptable salt form, in an ophthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, in free or ophthalmologically acceptable salt form, in combination or association with an ophthalmologically acceptable diluent or carrier.

Optionally, the PDE1 inhibitor may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 Inhibitor of the Invention, in free or pharmaceutically acceptable salt form, such that amount of the agent known to lower intraocular pressure and the amount of the PDE1 inhibitor in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with a PDE1 inhibitor may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 Inhibitor of the Invention and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine. For example, the invention provides ophthalmic formulations comprising a PDE-1 Inhibitor of the Invention together with bimatoprost, abrimonidine, brimonidine, timolol, or combinations thereof, in free or ophthamologically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic agonist selective for a particular receptor subtype such as $M_1$-$M_5$.

The PDE 1 inhibitor may be administered in the form of an ophthalmic composition, which includes an ophthalmic solution, cream or ointment. The ophthalmic composition may additionally include an intraocular-pressure lowering agent.

In yet another example, the PDE-1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, in free or pharmaceutically acceptable salt form, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously administering therapeutically effective amounts of:
  (i) a PDE 1 Inhibitor of the invention, in free or pharmaceutically acceptable salt form; and
  (ii) an antipsychotic, e.g.,
    Typical antipsychotics, e.g.,
      Butyrophenones, e.g. Haloperidol (Haldol, Serenace), Droperidol (Droleptan);
      Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);
      Thioxanthenes, e.g., Chlorprothixene, Flupenthixol (Depixol, Fluanxol), Thiothixene (Navane), Zuclopenthixol (Clopixol, Acuphase);
    Atypical antipsychotics, e.g.,
      Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine,
    in free or pharmaceutically acceptable salt form, to a patient in need thereof.

In a particular embodiment, the Compounds of the Invention are particularly useful for the treatment or prophylaxis of schizophrenia.

Compounds of the Invention, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, in free or pharmaceutically acceptable salt form, to the eye of a patient in need thereof.

In yet another aspect, the invention provides a method for the treatment or prophylaxis of traumatic brain injury comprising administering a therapeutically effective amount of a PDE1 inhibitor of the invention, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury. Abnormal calcium homeostasis is believed to be a critical component of the progression of secondary injury in both grey and white matter. For a review of TBI, see Park et al., CMAJ (2008) 178(9):1163-1170, the contents of which are incorporated herein in their entirety. Studies have shown that the cAMP-PKA signaling cascade is downregulated after TBI and treatment of PDE IV inhibitors such as rolipram to raise or restore cAMP level improves histopathological outcome and decreases inflammation after TBI. As Compounds of the present invention is a PDE1 inhibitor, it is believed that these compounds are also useful for the treatment of TBI, e.g., by restoring cAMP level and/or calcium homeostasis after traumatic brain injury.

The present invention also provides
  (i) a Compound of the Invention, e.g., any of Formulae I-VIII or 1.1-1.111, as hereinbefore described, in free or pharmaceutically acceptable salt form for example for use in any method or in the treatment of any disease or condition as hereinbefore set forth,
  (ii) the use of a Compound of the Invention, e.g any of Formulae I-VIII or 1.1-1.111, as hereinbefore described, in free or pharmaceutically acceptable salt form, in the manufacture of a medicament for treating any disease or condition as hereinbefore set forth,
  (iii) a pharmaceutical composition comprising a Compound of the Invention, e.g., any of Formulae I-VIII or 1.1-1.111, as hereinbefore described, in free or pharmaceutically acceptable salt form, in combination or association with a pharmaceutically acceptable diluent or carrier, and
  (iv) a pharmaceutical composition comprising a Compound of the Invention, e.g., any of Formulae I-VIII or 1.1-1.111, as hereinbefore described, in free or pharmaceutically acceptable salt form, in combination or association with a pharmaceutically acceptable diluent or carrier for use in the treatment of any disease or condition as hereinbefore set forth.

Therefore, the invention provides use of a Compound of the Invention, e.g., any of Formulae I-VIII or 1.1-1.111, as hereinbefore described, in free or pharmaceutically acceptable salt form, or a Compound of the Invention in a pharmaceutical composition form, (the manufacture of a medicament) for the treatment or prophylactic treatment of the following diseases: Parkinson's disease, restless leg tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension or pulmonary hypertension, and/or sexual dysfunction; asthma, chronic obstructive pulmonary disease, and/or allergic rhinitis, as well as auto-immune and inflammatory diseases; and/or female sexual dysfunction, exercise amenorrhea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling.

The invention also provides use of a Compound of the Invention, in free or pharmaceutically acceptable salt form, (the manufacture of a medicament) for the treatment or prophylactic treatment of:
  a) glaucoma or elevated intraocular pressure,
  b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder, or
  c) traumatic brain injury.

The phrase "Compounds of the Invention" or "PDE 1 inhibitors of the Invention" encompasses any and all of the compounds disclosed herewith, e.g., an optionally substituted:
4,5,7,8-tetrahydro-(1H or 2H)-imidazo[1,2-a]pyrazolo[4,3-e]pyrimidine,
4,5,7,8-tetrahydro-(1H or 2H)-imidazo[1,2-a]pyrazolo[4,3-e]pyrimidine-4(5H)-one,
4,5,7,8-tetrahydro-(1H or 2H)-imidazo[1,2-a]pyrazolo[4,3-e]pyrimidine-4(5H)-thione,
4,5,7,8-tetrahydro-(1H or 2H)-imidazo[1,2-a]pyrazolo[4,3-e]pyrimidine-4(5H)-imine,
4,5,7,8,9-pentahydro-(1H or 2H)-pyrimido[1,2-a]pyrazolo[4,3-e]pyrimidine,
4,5,7,8,9-pentahydro-(1H or 2H)-pyrimido[1,2-a]pyrazolo[4,3-e]pyrimidine-4(5H)-one,
4,5,7,8,9-pentahydro-(1H or 2H)-pyrimido[1,2-a]pyrazolo[4,3-e]pyrimidine-4(5H)-thione,
4,5,7,8,9-pentahydro-(1H or 2H)-pyrimido[1,2-a]pyrazolo[4,3-e]pyrimidine-4(5H)-imine,
any of Formulae I-VIII or 1.1-1.111,
  in free or (pharmaceutically) salt form.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "pulmonary hypertension" is intended to encompass pulmonary arterial hypertension.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention are in particular useful for the treatment of Parkinson's disease, narcolepsy and female sexual dysfunction.

Compounds of the Invention, in free or pharmaceutically acceptable salt form, may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

The synthetic methods for various Compounds of the Present Invention are illustrated below. Other compounds of the Invention and their salts may be made using the methods as similarly described below and/or by methods similar to those generally described in the detailed description and by methods known in the chemical art.

Example 1

(6aR,9aS)-5,6a,7,8,9,9a-hexahydro-5-methyl-3-phenoxy-2-(4-(1H-pyrazol-1-yl)benzyl)-cyclopent[4,5]imidazo[1,2-a]pyrazolo[4,3-e]pyrimidin-4(2H)-one

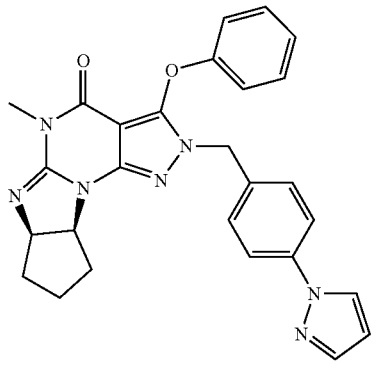 [SMILES: CN1C(=O)c2c(nn(Cc3ccc(-n4cccn4)cc3)c2Oc2ccccc2)N2C1=N[C@@H]1CCC[C@@H]12]

(a) 2-(4-(1H-pyrazol-1-yl)benzyl)-7-(4-methoxybenzyl)-5-methyl-2H-pyrazolo[3,4-d]pyrimidine-4,6(5H,7H)-dione A suspension of 7-(4-methoxybenzyl)-5-methyl-2H-pyrazolo[3,4-d]pyrimidine-4,6(5H,7H)-dione (667 mg, 2.33 mmol), 1-(4-(bromomethyl)phenyl)-1H-pyrazole (552 mg, 2.33 mmol) and $K_2CO_3$ (644 mg, 4.66 mmol) in DMF (20 mL) is stirred at room temperature overnight. Solvent is removed under reduced pressure. The obtained residue is treated with methylene chloride (400 mL), and then washed with water three times. The organic phase is evaporated to dryness to give 1.0 g of crude product, which is used in the next step without further purification. MS (ESI) m/z 443.2 [M+H]$^+$.

(b) 2-(4-(1H-pyrazol-1-yl)benzyl)-5-methyl-2H-pyrazolo[3,4-d]pyrimidine-4,6(5H,7H)-dione TFA (3.0 mL) is added into a suspension of 2-(4-(1H-pyrazol-1-yl)benzyl)-7-(4-methoxybenzyl)-5-methyl-2H-pyrazolo[3,4-d]pyrimidine-4,6(5H,7H)-dione (1.0 g, 2.3 mmol) in methylene chloride (6 mL) to give a tan solution, and then TFMSA (0.85 mL) is added. The reaction mixture is stirred at room temperature overnight, and then diluted with 100 mL of methylene chloride, followed by adding 50 mL of water to precipitate product out of solution. After filtration, the obtained solids are washed with water twice, and then dried under vacuum to give the first crop of crude product. The organic phase in the filtrate is washed with water twice, and then evaporated to remove solvents to the second crop of crude product. The obtained crude product is combined (0.94 g in total) and is used in the next step without further purification. MS (ESI) m/z 323.1 [M+H]$^+$.

(c) 2-(4-(1H-pyrazol-1-yl)benzyl)-6-((1R,2R)-2-hydroxycyclopentylamino)-5-methyl-2H-pyrazolo[3,4-d]pyrimidin-4(5H)-one DBU (1.2 mL, 7.9 mmol) is added into a suspension of crude 2-(4-(1H-pyrazol-1-yl)benzyl)-5-methyl-2H-pyrazolo[3,4-d]pyrimidine-4,6(5H,7H)-dione TFMSA salt (620 mg, 1.3 mmol) and BOP (1.7 g, 3.9 mmol) in THF (12 mL) to give a yellow solution. The mixture is stirred at room temperature for 5 min, and then (1R,2R)-2-aminocyclopentanol hydrochloride (542 mg, 3.9 mmol) is added. The reaction mixture is stirred at room temperature for 4 hours. After removal of solvent, the residue is treated with methylene chloride, and then washed with saturated $NaHCO_3$ aqueous solution three times. The organic phase is evaporated to dryness to give 2.1 g salt-containing crude product, which is used in the next step without further purification. MS (ESI) m/z 406.2 [M+H]$^+$.

(d) (6aR,9aS)-5,6a,7,8,9,9a-hexahydro-5-methyl-2-(4-(1H-pyrazol-1-yl)benzyl)-cyclopent[4,5]imidazo[1,2-a]pyrazolo[4,3-e]pyrimidin-4(2H)-one Thionyl chloride (180 μL, 2.47 mmol) is added dropwise to a solution of crude 2-(4-(1H-pyrazol-1-yl)benzyl)-6-((1R,2R)-2-hydroxycyclopentylamino)-5-methyl-2H-pyrazolo[3,4-d]pyrimidin-4(5H)-one (2.0 g, 4.9 mmol) in DMF (10 mL). The reaction mixture is stirred at room temperature for 20 min. DMF is removed under reduced pressure. The obtained residue is treated with methylene chloride (200 mL), and then washed with 5% $NaHCO_3$ aqueous solution three times (3×80 mL). The organic phase is evaporated to dryness to give 1.1 g crude product, which is used in the next step without further purification. MS (ESI) m/z 388.2 [M+H]$^+$.

(e) (6aR,9aS)-5,6a,7,8,9,9a-hexahydro-3-chloro-5-methyl-2-(4-(1H-pyrazol-1-yl)benzyl)-cyclopent[4,5]imidazo[1,2-a]pyrazolo[4,3-e]pyrimidin-4(2H)-one 1.0M LiHMDS (4.25 mL, 4.25 mml) in THF is added dropwise into a solution of crude (6aR,9aS)-5,6a,7,8,9,9a-hexahydro-5-methyl-2-(4-(1H-pyrazol-1-yl)benzyl)-cyclopent[4,5]imidazo[1,2-a]pyrazolo[4,3-e]pyrimidin-4(2H)-one (1.1 g) and hexachloroethane (403 mg, 1.7 mmol) in methylene chloride (20 mL). The reaction mixture is stirred at room temperature for 20 min, and then diluted with methylene chloride (130 mL), followed by washing with water four times (4×50 mL). The organic phase is evaporated to dryness to give 754 mg of crude product with 84% purity, which is used in the next step without further purification. MS (ESI) m/z 422.2 [M+H]$^+$.

(f) (6aR,9aS)-5,6a,7,8,9,9a-hexahydro-5-methyl-3-phenoxy-2-(4-(1H-pyrazol-1-yl)benzyl)-cyclopent[4,5]imidazo[1,2-a]pyrazolo[4,3-e]pyrimidin-4(2H)-one Crude (6aR,9aS)-5,6a,7,8,9,9a-hexahydro-3-chloro-5-methyl-2-(4-(1H-pyrazol-1-yl)benzyl)-cyclopent[4,5]imidazo[1,2-a]pyrazolo[4,3-e]pyrimidin-4(2H)-one (50 mg), phenol (45 mg, 0.47 mmol) and $Cs_2CO_3$ (77 mg, 0.24 mmol) are placed in a microwave vial, and then dioxane (1 mL) is added. The vial is sealed and heated in a Biotage microwave instrument at 130° C. for 40 min. The reaction mixture is then purified with a semi-preparative HPLC to give 11 mg of product as off-white solid (purity: 97%). MS (ESI) m/z 480.2 [M+H]$^+$.

Example 2

(6aR,9aS)-5,6a,7,8,9,9a-hexahydro-3-(4-fluorophenoxy)-5-methyl-2-(4-(pyridin2-yl)benzyl)-cyclopent[4,5]imidazo[1,2-a]pyrazolo[4,3-e]pyrimidin-4(2H)-one

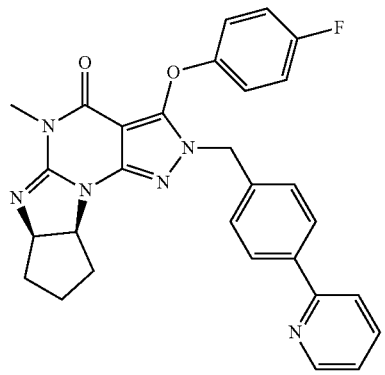 [SMILES: CN1C(=O)c2c(nn(Cc3ccc(-c4ccccn4)cc3)c2Oc2ccc(F)cc2)N2C1=N[C@@H]1CCC[C@@H]12]

The synthesis method is analogous to example 1 wherein 2-(4-(chloromethyl)phenyl)pyridine is added in step (a) instead of 1-(4-(bromomethyl)phenyl)-1H-pyrazole; and 4-fluorophenol is added in step (f) instead of phenol. MS (ESI) m/z 509.2 [M+H]$^+$

Example 3

7,8-dihydro-5,7,7-trimethyl-3-phenoxy-2-(4-(6-Fluoro-pyridin-2-yl)-benzyl)-imidazo[1,2-a]pyrazolo[4,3-e]pyrimidin-4(2H)-one

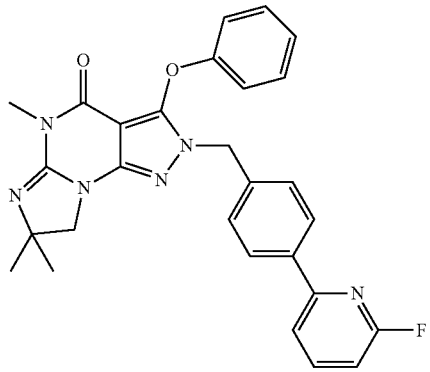 [SMILES: CN1C(=O)c2c(nn(Cc3ccc(-c4cccc(F)n4)cc3)c2Oc2ccccc2)N2CC(C)(C)N=C12]

The synthesis method is analogous to example 1 wherein 2-(4-(chloromethyl)phenyl)-6-fluoropyridine is added in step (a) instead of 1-(4-(bromomethyl)phenyl)-1H-pyrazole; and 2-amino-2-methylpropan-1-ol is added in step (c) instead of (1R,2R)-2-aminocyclopentanol hydrochloride. MS (ESI) m/z 497.2 [M+H]$^+$

Example 4

(6aR,9aS)-5,6a,7,8,9,9a-hexahydro-5-methyl-3-(4-fluorophenoxy)-2-(4-(1H-pyrazol-1-yl)benzyl)-cyclopent[4,5]imidazo[1,2-a]pyrazolo[4,3-e]pyrimidin-4(2H)-one

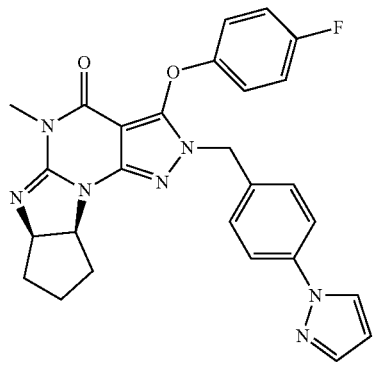 [SMILES: CN1C(=O)c2c(nn(Cc3ccc(-n4cccn4)cc3)c2Oc2ccc(F)cc2)N2C1=N[C@@H]1CCC[C@@H]12]

The synthesis method is analogous to example 1 wherein 4-fluorophenol is added in step (f) instead of phenol. MS (ESI) m/z 498.3 [M+H]$^+$

Example 5

(6aR,9aS)-5,6a,7,8,9,9a-hexahydro-3-(cyclohexyloxy)-5-methyl-2-(4-(6-fluoro-pyridin-2-yl)-benzyl)-cyclopent[4,5]imidazo[1,2-a]pyrazolo[4,3-e]pyrimidin-4(2H)-one

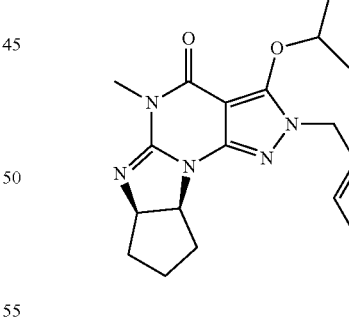

(6aR,9aS)-5,6a,7,8,9,9a-hexahydro-3-chloro-5-methyl-2-(4-(6-fluoro-pyridin-2-yl)-benzyl)-cyclopent[4,5]imidazo[1,2-a]pyrazolo[4,3-e]pyrimidin-4(2H)-one (25 mg, 0.055 mmol), cyclohexanol (0.5 mL) and Cs$_2$CO$_3$ (27 mg, 0.083 mmol) are placed in a microwave vial. The vial is sealed and heated in a Biotage microwave instrument at 140° C. for an hour. The reaction mixture is then purified with a semi-preparative HPLC to give 14 mg of product as white solids (purity: 98%). MS (ESI) m/z 515.2 [M+H]$^+$.

Example 6

(6aR,9aS)-5,6a,7,8,9,9a-hexahydro-3-(cyclopentyloxy)-5-methyl-2-(4-(6-fluoro-pyridin-2-yl)-benzyl)-cyclopent[4,5]imidazo[1,2-a]pyrazolo[4,3-e]pyrimidin-4(2H)-one

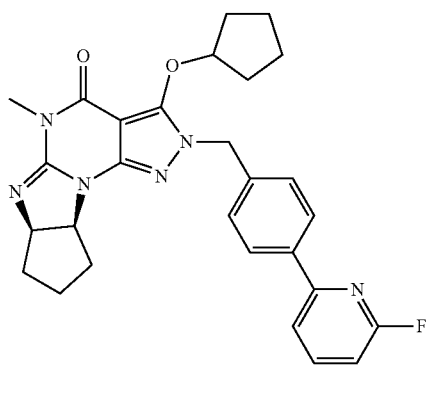 [SMILES: CN1C(=O)c2c(nn(Cc3ccc(-c4cccc(F)n4)cc3)c2OC2CCCC2)N2C1=N[C@@H]1CCC[C@@H]12]

The synthesis method is analogous to Example 5 wherein cyclopentanol is added instead of cyclohexanol. MS (ESI) m/z 501.3 [M+H]+

Example 7

(6aR,9aS)-5,6a,7,8,9,9a-hexahydro-3-isobutoxy-5-methyl-2-(4-(6-fluoro-pyridin-2-yl)-benzyl)-cyclopent[4,5]imidazo[1,2-a]pyrazolo[4,3-e]pyrimidin-4(2H)-one

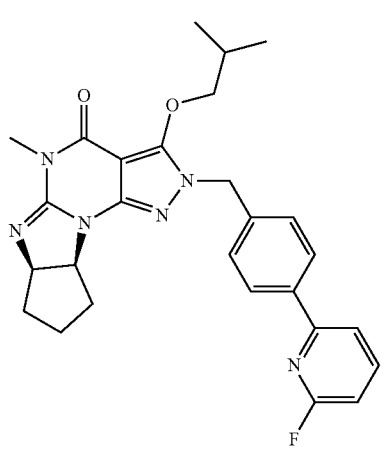 [SMILES: CC(C)COc1c2c(nn1Cc1ccc(-c3cccc(F)n3)cc1)N1C(=N[C@@H]3CCC[C@@H]31)N(C)C2=O]

The synthesis method is analogous to Example 5 wherein 2-methylpropan-1-ol is added instead of cyclohexanol. MS (ESI) m/z 489.3 [M+H]+

Example 8

(6aR,9aS)-5,6a,7,8,9,9a-hexahydro-3-isopropoxy-5-methyl-2-(4-(6-fluoro-pyridin-2-yl)-benzyl)-cyclopent[4,5]imidazo[1,2-a]pyrazolo[4,3-e]pyrimidin-4(2H)-one

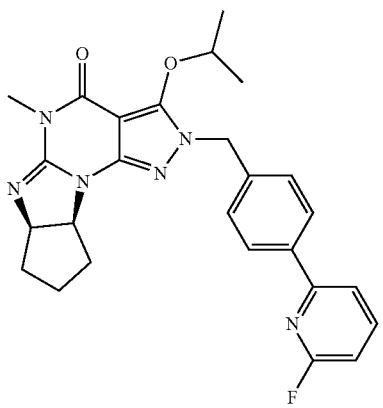 [SMILES: CC(C)Oc1c2c(nn1Cc1ccc(-c3cccc(F)n3)cc1)N1C(=N[C@@H]3CCC[C@@H]31)N(C)C2=O]

The synthesis method is analogous to Example 5 wherein propan-2-ol is added instead of cyclohexanol. MS (ESI) m/z 475.2 [M+H]+

Example 9

(6aR,9aS)-5,6a,7,8,9,9a-hexahydro-3-phenoxy-5-methyl-2-(4-(6-fluoro-pyridin-2-yl)-benzyl)-cyclopent[4,5]imidazo[1,2-a]pyrazolo[4,3-e]pyrimidin-4(2H)-one

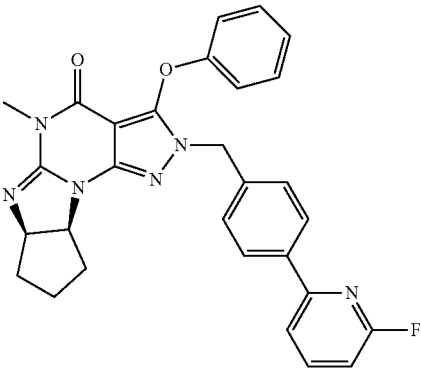 [SMILES: CN1C(=O)c2c(nn(Cc3ccc(-c4cccc(F)n4)cc3)c2Oc2ccccc2)N2C1=N[C@@H]1CCC[C@@H]12]

(6aR,9aS)-5,6a,7,8,9,9a-hexahydro-3-chloro-5-methyl-2-(4-(6-fluoro-pyridin-2-yl)-benzyl)-cyclopent[4,5]imidazo[1,2-a]pyrazolo[4,3-e]pyrimidin-4(2H)-one (26 mg, 0.058 mmol), phenol (10.8 mg, 0.12 mmol) and $K_2CO_3$ (24 mg, 0.17 mmol) are placed in a microwave vial, and then dioxane (0.5 mL) is added. The vial is sealed and heated in a Biotage microwave instrument at 150° C. for three hours. The reaction mixture is then purified with a semi-preparative HPLC to give 21 mg of product as white solids (purity: 98.6%). MS (ESI) m/z 509.2 [M+H]+.

Example 10

(6aR,9aS)-5,6a,7,8,9,9a-hexahydro-3-(4-fluorophenoxy)-5-methyl-2-(4-(6-fluoro-pyridin-2-yl)-benzyl)-cyclopent[4,5]imidazo[1,2-a]pyrazolo[4,3-e]pyrimidin-4(2H)-one

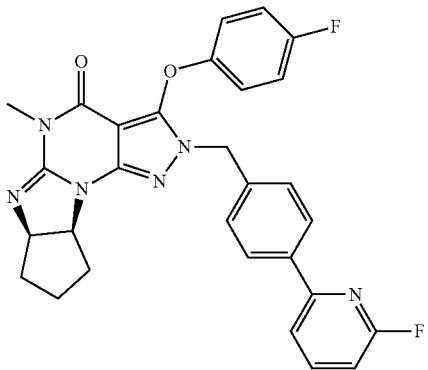 [SMILES: CN1C(=O)c2c(nn(Cc3ccc(-c4cccc(F)n4)cc3)c2Oc2ccc(F)cc2)N2C1=N[C@@H]1CCC[C@@H]12]

The synthesis method is analogous to Example 9 wherein 4-fluorophenol is added instead of phenol. MS (ESI) m/z 527.2 [M+H]$^+$

Example 11

(6aR,9aS)-5,6a,7,8,9,9a-hexahydro-3-(3-chlorophenoxy)-5-methyl-2-(4-(6-fluoro-pyridin-2-yl)-benzyl)-cyclopent[4,5]imidazo[1,2-a]pyrazolo[4,3-e]pyrimidin-4(2H)-one

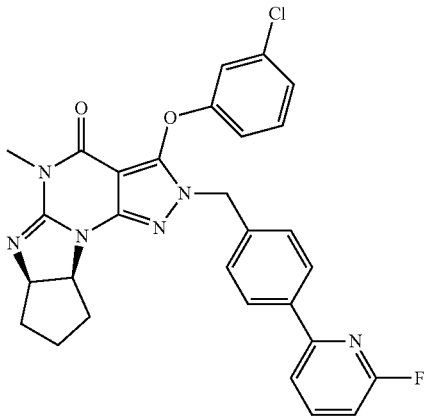 [SMILES: CN1C(=O)c2c(nn(Cc3ccc(-c4cccc(F)n4)cc3)c2Oc2cccc(Cl)c2)N2C1=N[C@@H]1CCC[C@@H]12]

The synthesis method is analogous to Example 9 wherein 3-chlorophenol is added instead of phenol. MS (ESI) m/z 543.2 [M+H]$^+$

Example 12

Measurement of PDE1B Inhibition In Vitro Using IMAP Phosphodiesterase Assay Kit Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM CaCl$_2$, 10 U/ml of calmodulin (Sigma P2277), 10 mM Tris-HCl pH 7.2, 10 mM MgCl$_2$, 0.1% BSA, 0.05% NaN$_3$) to yield a final concentration of 1.25 mU/ml. 99 μl of diluted enzyme solution is added into each well in a flat bottom 96-well polystyrene plate to which 1 μl of test compound dissolved in 100% DMSO is added. Selected Compounds of the Invention are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. IC$_{50}$ values are determined by measuring enzyme activity in the presence of 8 to 16 concentrations of compound ranging from 0.0037 nM to 80,000 nM and then plotting drug concentration versus ΔmP, which allows IC$_{50}$ values to be estimated using nonlinear regression software (XLFit; IDBS, Cambridge, Mass.).

The Compounds of the Invention may be selected and tested in an assay as described or similarly described herein for PDE1 inhibitory activity. The exemplified compounds of the invention generally have IC$_{50}$ values of less than or equal to 100 nM, some less than 10 nM, some less than 1 nM, against PDE1A and/or PDE1B.

Example 13

PDE1 Inhibitor Effect on Sexual Response in Female Rats

The effect of PDE1 inhibitors on Lordosis Response in female rats may be measured as described in Mani, et al., Science (2000) 287: 1053. Ovariectomized and cannulated wild-type rats are primed with 2 µg estrogen followed 24 hours later by intracerebroventricular (icv) injection of progesterone (2 µg), PDE1 inhibitors of the present invention (0.1 mg, 1.0 mg or 2.5 mg) or sesame oil vehicle (control). The rats may be tested for lordosis response in the presence of male rats. Lordosis response is quantified by the lordosis quotient (LQ=number of lordosis/10 mounts×100).

What is claimed is:

1. A PDE 1 inhibitor compound, wherein said compound is a compound of Formula I:

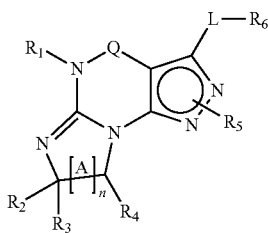

Formula I wherein
- (i) Q is —C(=S)—, —C(=N($R_{20}$))—, —C(=O)— or $CH_2$;
- (ii) L is a —O—;
- (iii) $R_1$ is H or $C_{1-4}$alkyl;
- (iv) $R_4$ is H or $C_{1-4}$alkyl and $R_2$ and $R_3$ are, independently:
  H,
  $C_{1-6}$alkyl optionally substituted with halo or hydroxy,
  aryl,
  heteroaryl,
  (optionally hetero)aryl$C_{1-6}$alkyl, or
  $R_2$ and $R_3$ together with the carbon to which they are attached form a 3- to 6-membered ring; or
  $R_2$ is H and $R_3$ and $R_4$ together form a di-, tri- or tetra-methylene bridge;
- (v) $R_5$ is
  a) -D-E-F, wherein:
    D is a single bond, $C_{1-4}$alkylene or —C(=O)—;
    E is a single bond, $C_{1-4}$alkylene, arylene, aryl$C_{1-4}$alkylene or heteroarylene; and
    F is
    H,
    aryl,
    heteroaryl,
    halo,
    $C_{1-4}$alkyl,
    halo$C_{1-4}$alkyl,
    halo$C_{1-4}$alkoxy,
    $C_{1-4}$alkoxy,
    —C(O)—$R_{15}$,
    —N($R_{16}$)($R_{17}$),
    —S(O)$_2$$R_{21}$,
    $C_{3-7}$cycloalkyl or
    heteroC$_{3-7}$cycloalkyl;
    wherein D, E and F are independently and optionally substituted with one or more group selected from:
    halo,
    $C_{1-4}$alkyl,
    halo$C_{1-4}$alkyl, and
    $C_{1-4}$alkoxy;
  b) heteroaryl$C_{1-4}$alkyl optionally substituted with halo$C_{1-4}$alkyl;
  or
  c) attached to one of the nitrogen atoms on the pyrazolo portion of Formula I and is a moiety of Formula A

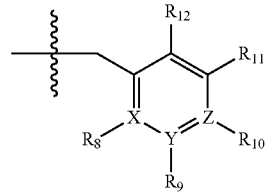

Formula A wherein X, Y and Z are, independently, N or C, and $R_8$, $R_9$, $R_{11}$ and $R_{12}$ are independently H, halogen, —$C_{1-4}$alkyl-N($R_{22}$)($R_{23}$), or —$C_{1-4}$alkyl-heterC$_{3-5}$cycloalkyl, and $R_{10}$ is:
  hydrogen,
  halogen,
  $C_{1-4}$alkyl,
  halo$C_{1-4}$alkyl,
  halo$C_{1-4}$alkoxy,
  $C_{1-4}$alkoxy,
  $C_{3-7}$cycloalkyl,
  hetC$_{3-7}$cycloalkyl,
  $C_{1-4}$haloalkyl,
  aryl,
  heteroaryl,
  arylcarbonyl,
  $C_{1-4}$alkylsulfonyl,
  aminosulfonyl,
  heteroarylcarbonyl,
  $C_{1-4}$alkylcarbonyl,
  $C_{1-4}$alkoxycarbonyl,
  —C(O)OH,
  halo$C_{1-4}$alkoxycarbony,
  —C(O)N($R_{18}$)($R_{19}$), or
  —$C_{1-4}$alkyl-N($R_{18}$)($R_{19}$),
  wherein the aryl, heteroaryl, cycloalkyl and heterocycloalkyl are independently and optionally substituted with one or more group selected from halo, $C_{1-4}$alkyl, $C_{1-4}$alkoxy, $C_{1-4}$haloalkyl and —SH; provided that when X, Y, or Z is nitrogen, $R_8$, $R_9$, or $R_{10}$, respectively, is not present;
- (vi) $R_6$ is
  $C_{1-4}$alkyl,
  $C_{3-7}$cycloalkyl,
  aryl,
  heteroaryl, or
  aryl$C_{1-4}$alkyl,
  wherein the aryl or heteroaryl is optionally substituted with one or more group selected from halo, hydroxy, $C_{1-6}$alkyl, $C_{1-6}$alkoxy and $C_{3-8}$cycloalkyl,
- (vii) n=0 or 1;
- (viii) when n=1, A is —C($R_{13}R_{14}$)—, wherein $R_{13}$ and $R_{14}$, are, independently, H, $C_{1-4}$alkyl, aryl, heteroaryl, (optionally hetero)aryl$C_{1-4}$alkoxy or (optionally hetero)arylC$_{1-4}$alkyl or R$_{13}$ or R$_{14}$ can form a di-, tri- or tetramethylene bridge with R$_2$ or R$_4$;
(ix) R$_{15}$ is C$_{1-4}$alkyl, haloC$_{1-4}$alkyl, —OH, —OC$_{1-4}$alkyl, aryl or —N(R$_{16}$)(R$_{17}$);
(x) R$_{16}$ and R$_{17}$ are independently H or C$_{1-4}$alkyl;
(xi) R$_{18}$ and R$_{19}$ are independently
H,
C$_{1-4}$alky,
C$_{3-8}$cycloalkyl,
heteroC$_{3-8}$cycloalkyl,
aryl, or
heteroaryl,
wherein said aryl or heteroaryl is optionally substituted with one or more group selected from:
halo,
hydroxy,
C$_{1-6}$alkyl,
haloC$_{1-6}$alkyl,
C$_{1-6}$alkoxy,
aryl,
heteroaryl, and
C$_{3-8}$cycloalkyl;
(xii) R$_{20}$ is H, C$_{1-4}$alkyl or C$_{3-7}$cycloalkyl;
(xiii) R$_{21}$ is C$_{1-6}$alkyl or —N(R$_{18}$)(R$_{19}$);
(xiv) R$_{22}$ and R$_{23}$ are independently H or C$_{1-4}$alkyl,
in free or salt form.

2. A PDE1 inhibitor compound, wherein said compound is selected form any one of the following:
A) a Compound of Formula II:

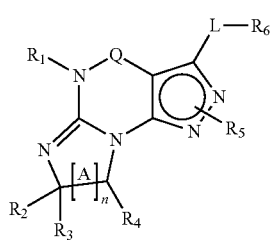

Formula II wherein
(i) Q is —C(=S)—, —C(=N(R$_{20}$))—, —C(=O)— or CH$_2$;
(ii) L is a —O—;
(iii) R$_1$ is H or C$_{1-4}$alkyl;
(iv) R$_4$ is H or C$_{1-4}$alkyl and R$_2$ and R$_3$ are, independently:
H,
C$_{1-6}$alkyl optionally substituted with halo or hydroxy,
aryl,
heteroaryl,
(optionally hetero)arylC$_{1-6}$alkoxy, or
(optionally hetero)arylC$_{1-6}$alkyl, or
R$_2$ and R$_3$ together with the carbon to which they are attached form a 3- to 6-membered ring; or
R$_2$ is H and R$_3$ and R$_4$ together form a di-, tri- or tetramethylene bridge;
(v) R$_5$ is
a) -D-E-F, wherein
D is C$_{1-4}$alkylene;
E is arylene; and
F is aryl, heteroaryl, C$_{3-7}$cycloalkyl, or heteroC$_{3-7}$cycloalkyl, wherein F is optionally substituted with one or more halo or C$_{1-6}$alkyl; or
b) attached to one of the nitrogen atoms on the pyrazolo portion of Formula II and is a moiety of Formula A

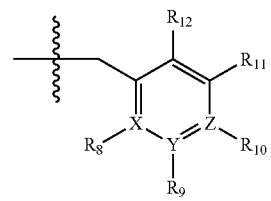

Formula A wherein X, Y and Z are, independently, N or C, and R$_8$, R$_9$, R$_{11}$ and R$_{12}$ are independently H, halogen, and R$_{10}$ is C$_{3-7}$cycloalkyl, hetC$_{3-7}$cycloalkyl, aryl, or heteroaryl, wherein the aryl, heteroaryl, cycloalkyl and heterocycloalkyl are independently and optionally substituted with one or more halo, C$_{1-4}$alkyl, provided that when X, Y, or Z is nitrogen, R$_8$, R$_9$, or R$_{10}$, respectively, is not present;
(vi) R$_6$ is
C$_{1-4}$alkyl,
C$_{3-7}$cycloalkyl,
aryl,
heteroaryl,
arylC$_{1-4}$alkyl,
wherein the aryl or heteroaryl is optionally substituted with one or more halo, hydroxy, C$_{1-6}$alkyl, C$_{1-6}$alkoxy, C$_{3-8}$cycloalkyl;
(vii) n=0 or 1;
(viii) when n=1, A is —C(R$_{13}$R$_{14}$)—, wherein R$_{13}$ and R$_{14}$, are, independently, H or C$_{1-4}$alkyl, aryl, heteroaryl, (optionally hetero)arylC$_{1-4}$alkoxy, (optionally hetero)arylC$_{1-4}$alkyl or R$_{13}$ or R$_{14}$ can form a di-, tri- or tetramethylene bridge with R$_2$ or R$_4$;
(ix) R$_{20}$ is H, C$_{1-4}$alkyl or C$_{3-7}$cycloalkyl,
in free or salt form;
B) a compound of Formula III:

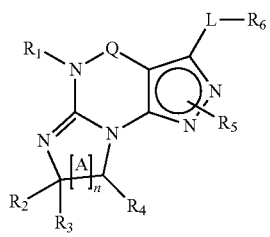

Formula III wherein
(i) Q is —C(=S)—, —C(=N(R$_{20}$))—, —C(=O)— or CH$_2$;
(ii) L is a —O—;
(iii) R$_1$ is H or C$_{1-4}$alkyl;
(iv) R$_4$ is H or C$_{1-4}$alkyl and R$_2$ and R$_3$ are, independently:
H,
C$_{1-6}$alkyl optionally substituted with halo or hydroxy,
aryl,
heteroaryl,
(optionally hetero)arylC$_{1-6}$alkoxy,
(optionally hetero)arylC$_{1-6}$alkyl, or
R$_2$ and R$_3$ together with the carbon to which they are attached form a 3- to 6-membered ring; or
R$_2$ is H and R$_3$ and R$_4$ together form a di-, tri- or tetramethylene bridge;

(v) $R_5$ is
a) -D-E-F, wherein
D is $C_{1-4}$alkylene;
E is arylene; and
F is aryl, heteroaryl, $C_{3-7}$cycloalkyl, or heteroC$_{3-7}$cycloalkyl, wherein F is optionally substituted with one or more halo or $C_{1-6}$alkyl; or
b) attached to one of the nitrogen atoms on the pyrazolo portion of Formula III and is a moiety of Formula A

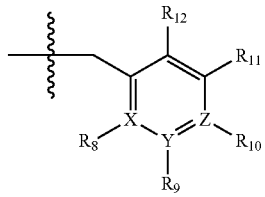

Formula A wherein X, Y and Z are, independently, N or C, and $R_8$, $R_9$, $R_{11}$ and $R_{12}$ are independently H or halogen, and $R_{10}$ is $C_{3-7}$cycloalkyl, hetC$_{3-7}$cycloalkyl, aryl, or heteroaryl, wherein the aryl, heteroaryl, cycloalkyl and heterocycloalkyl are independently and optionally substituted with one or more halo or $C_{1-4}$alkyl,
provided that when X, Y, or Z is nitrogen, $R_8$, $R_9$, or $R_{10}$, respectively, is not present;
(vi) $R_6$ is:
$C_{1-4}$alkyl,
$C_{3-7}$cycloalkyl,
aryl,
heteroaryl,
wherein the aryl or heteroaryl is optionally substituted with one or more halo, hydroxy or $C_{1-6}$alkyl,
(vii) n=0 or 1;
(viii) when n=1, A is —C($R_{13}R_{14}$)—, wherein $R_{13}$ and $R_{14}$, are, independently, H or $C_{1-4}$alkyl, aryl, heteroaryl, (optionally hetero)arylC$_{1-4}$alkoxy, (optionally hetero)arylC$_{1-4}$alkyl or $R_{13}$ or $R_{14}$ can form a di-, tri- or tetramethylene bridge with $R_2$ or $R_4$;
(i) $R_{20}$ is H, $C_{1-4}$alkyl or $C_{3-7}$cycloalkyl,
in free or salt form;
C) a compound of Formula IV:

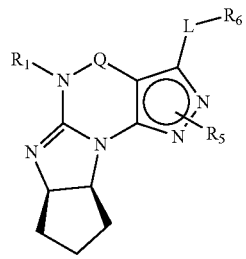

Formula IV wherein:
(i) Q is —C(=S)—, —C(=N($R_{20}$))—, —C(=O)— or CH$_2$;
(ii) L is a —O—;
(iii) $R_1$ is H or $C_{1-4}$alkyl;

(iv) $R_5$ is
a) -D-E-F, wherein
D is $C_{1-4}$alkylene;
E is arylene;
F is aryl, heteroaryl, $C_{3-7}$cycloalkyl, or heteroC$_{3-7}$cycloalkyl, wherein F is optionally substituted with one or more halo or $C_{1-6}$alkyl; or
b) attached to one of the nitrogen atoms on the pyrazolo portion of Formula IV and is a moiety of Formula A

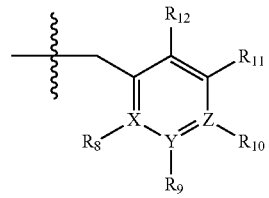

Formula A wherein X, Y and Z are, independently, N or C, and $R_8$, $R_9$, $R_{11}$ and $R_{12}$ are independently H or halogen, and $R_{10}$ is $C_{3-7}$cycloalkyl, hetC$_{3-7}$cycloalkyl, aryl, or heteroaryl, wherein the aryl, heteroaryl, cycloalkyl and heterocycloalkyl are independently and optionally substituted with one or more halo, $C_{1-4}$alkyl, provided that when X, Y, or Z is nitrogen, $R_8$, $R_9$, or $R_{10}$, respectively, is not present;
(v) $R_6$ is:
$C_{1-4}$alkyl,
$C_{3-7}$cycloalkyl,
aryl,
heteroaryl,
wherein the aryl or heteroaryl is optionally substituted with one or more halo, hydroxy or $C_{1-6}$alkyl,
(ii) $R_{20}$ is H, $C_{1-4}$alkyl or $C_{3-7}$cycloalkyl,
in free or salt form;
D) a compound of Formula V:

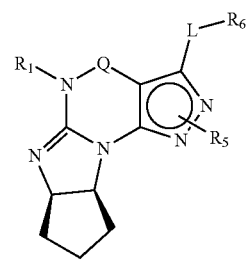

Formula V wherein:
(i) Q is —C(=O)—;
(ii) L is —O—;
(iii) $R_1$ is $C_{1-4}$alkyl;
(iv) $R_5$ is attached to one of the nitrogen atoms on the pyrazolo portion of Formula V and is a moiety of Formula A

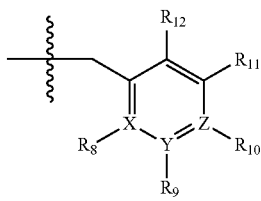

Formula A wherein X, Y and Z are C, and $R_8$, $R_9$, $R_{11}$ and $R_{12}$ are H, and $R_{10}$ is:
hetC$_{3-7}$cycloalkyl,
aryl, or
heteroaryl,
wherein the aryl, heteroaryl, cycloalkyl and heterocycloalkyl are independently and optionally substituted with one or more halo, C$_{1-4}$alkyl;
(v) $R_6$ is
C$_{3-7}$cycloalkyl,
aryl,
heteroaryl,
arylC$_{1-4}$alkyl,
wherein the aryl or heteroaryl is optionally substituted with one or more halo, hydroxy, C$_{1-6}$alkyl, C$_{1-6}$alkoxy, C$_{3-8}$cycloalkyl,
in free or salt form;
E) a compound of Formula VI:

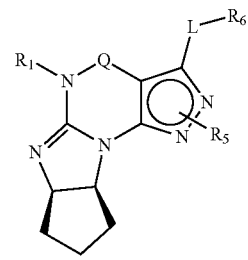

Formula VI wherein:
(i) Q is —C(=O)—;
(ii) L is —O—;
(iii) $R_1$ is C$_{1-4}$alkyl;
(iv) $R_5$ is attached to one of the nitrogen atoms on the pyrazolo portion of Formula VI and is a moiety of Formula A

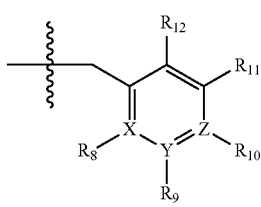

Formula A wherein X, Y and Z are C, and $R_8$, $R_9$, $R_{11}$ and $R_{12}$ are H, and $R_{10}$ is selected from piperidinyl, pyrrolidinyl, pyridyl, diazolyl, 6-fluoropyrid-2-yl, 1-methylpyrrolidin-3-yl, 1-methylpyrrolidin-2-yl, 1-ethylpiperidin-1-yl or 1-methylpiperidin-2-yl;

(v) $R_6$ is
C$_{3-7}$cycloalkyl,
aryl,
heteroaryl,
arylC$_{1-4}$alkyl,
wherein the aryl or heteroaryl is optionally substituted with one or more halo, hydroxy, C$_{1-6}$alkyl, C$_{1-6}$alkoxy, C$_{3-8}$cycloalkyl,
in free or salt form;
F) a compound of Formula VII:

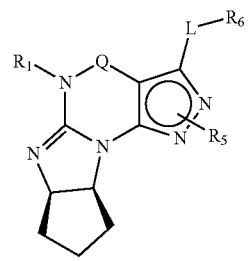

Formula VII wherein:
(i) Q is —C(=O)—;
(ii) L is —O—;
(iii) $R_1$ is C$_{1-4}$alkyl;
(iv) $R_5$ is attached to one of the nitrogen atoms on the pyrazolo portion of Formula VII and is a moiety of Formula A

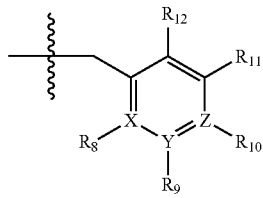

Formula A wherein X, Y and Z are C, and $R_8$, $R_9$, $R_{11}$ and $R_{12}$ are H, and $R_{10}$ is selected from piperidinyl, pyrrolidinyl, pyridyl, diazolyl, 6-fluoropyrid-2-yl, 1-methylpyrrolidin-3-yl, 1-methylpyrrolidin-2-yl, 1-ethylpiperidin-1-yl or 1-methylpiperidin-2-yl;
(v) $R_6$ is selected from cyclopentyl, cyclohexyl, phenyl, 3-chlorophenyl or 4-fluorophenyl,
in free or salt form;
G) a compound of Formula VIII:

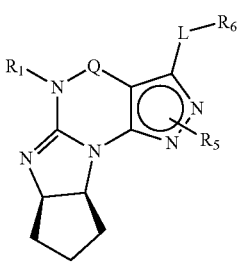

Formula VIII wherein:
 (i) Q is —C(=O)—;
 (ii) L is —O—;
 (iii) $R_1$ is $C_{1-4}$alkyl;
 (iv) $R_5$ is attached to one of the nitrogen atoms on the pyrazolo portion of Formula VIII and is a moiety of Formula A

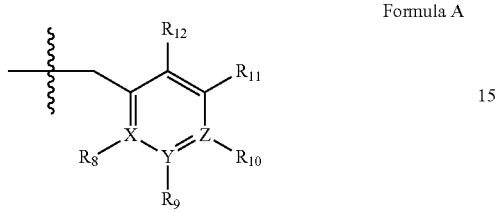

Formula A wherein X, Y and Z are C, and $R_8$, $R_9$, $R_{11}$ and $R_{12}$ are H, and $R_{10}$ is pyrid-2-yl, 6-fluoropyrid-2-yl, 1-methylpyrrolidin-3-yl, 1-methylpyrrolidin-2-yl, 1-ethylpiperidin-1-yl or 1-methylpiperidin-2-yl;
 (v) $R_6$ is phenyl or 4-fluorophenyl,
in free or salt form.

3. The Compound according to claim 1, wherein $R_{10}$ is selected from any of 5-fluoropyrid-2-yl, 6-fluoropyrid-2-yl, 3-fluoropyrid-2-yl, 4-fluoropyrid-2-yl, in free or salt form.

4. The Compound according to claim 1, wherein said compound is selected from any of the following:

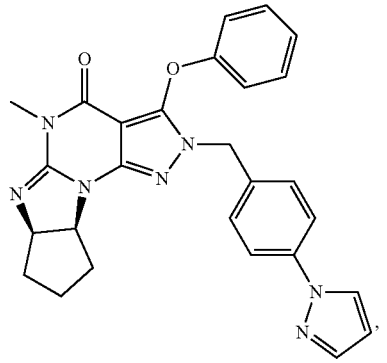

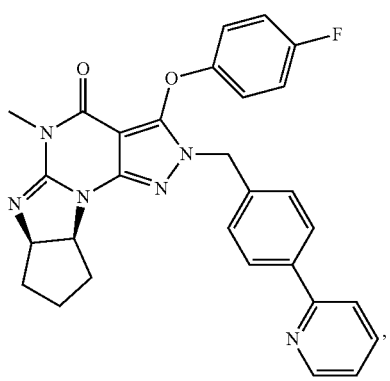

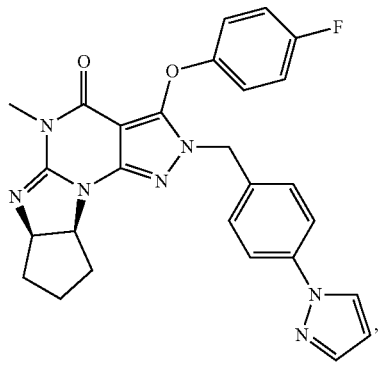

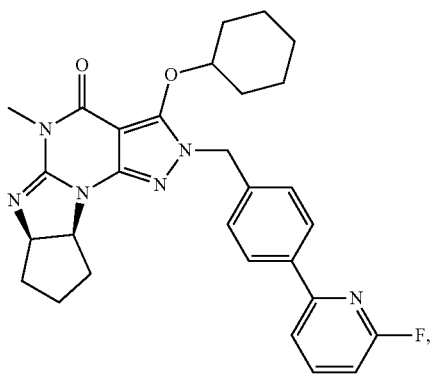

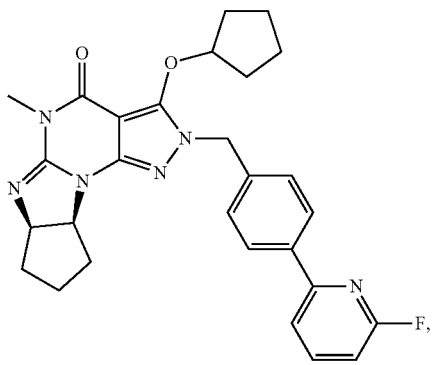

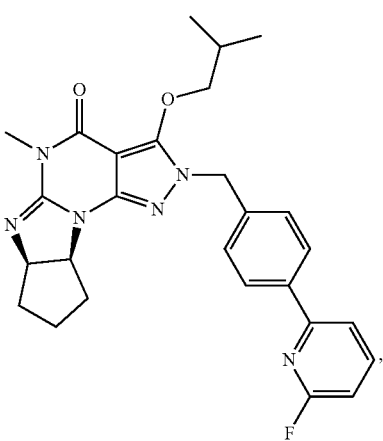

-continued

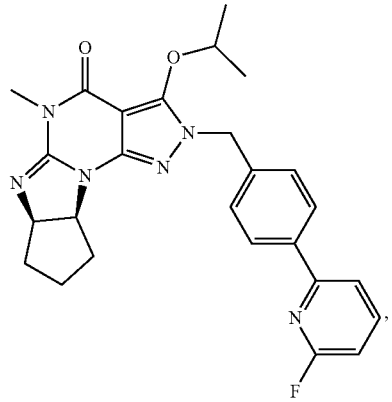

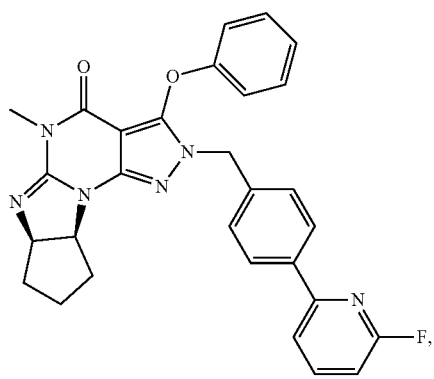

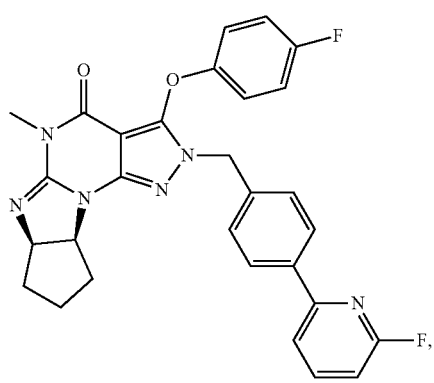

-continued

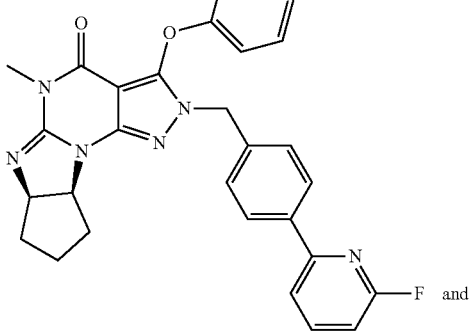
and

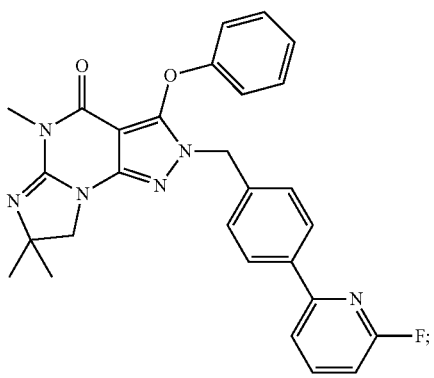

in free or salt form.

5. A pharmaceutical composition comprising a compound according to claim 1, in free or pharmaceutically acceptable salt form, in admixture with a pharmaceutically acceptable diluent or carrier.

6. The compound according claim 1, wherein said compound is a compound of Formula V:

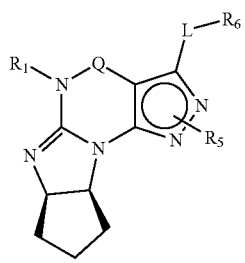

Formula V wherein:
(i) Q is —C(=O)—;
(ii) L is —O—;
(iii) $R_1$ is $C_{1-4}$alkyl;
(iv) $R_5$ is attached to one of the nitrogen atoms on the pyrazolo portion of Formula V and is a moiety of Formula A Formula A

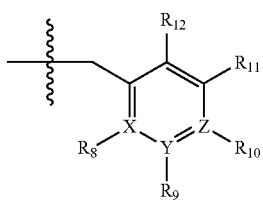

wherein X, Y and Z are C, and $R_8$, $R_9$, $R_{11}$ and $R_{12}$ are H, and $R_{10}$ is:
het$C_{3-7}$cycloalkyl,
aryl, or
heteroaryl,
  wherein the aryl, heteroaryl, cycloalkyl and heterocycloalkyl are independently and optionally substituted with one or more halo,
$C_{1-4}$alkyl;
(v) $R_6$ is
$C_{3-7}$cycloalkyl,
aryl,
heteroaryl,
aryl$C_{1-4}$alkyl,
  wherein the aryl or heteroaryl is optionally substituted with one or more halo, hydroxy, $C_{1-6}$alkyl, $C_{1-6}$alkoxy, $C_{3-8}$cycloalkyl,
in free or salt form.

7. The Compound according to claim 1, wherein $R_5$ is -D-E-F and D is $C_{1-4}$alkylene, E is arylene, and F is heteroaryl optionally substituted with one or more group selected from halo, $C_{1-4}$alkyl, halo$C_{1-4}$alkyl, and $C_{1-4}$alkoxy, in free or salt form.

8. The compound according to claim 1, wherein said compound is selected from:

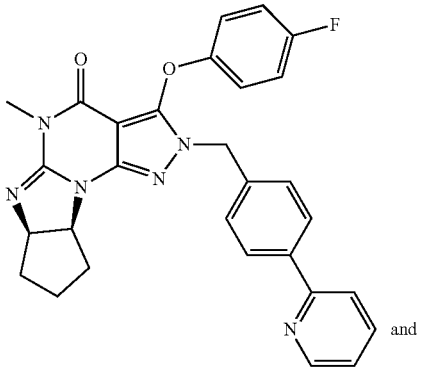

and

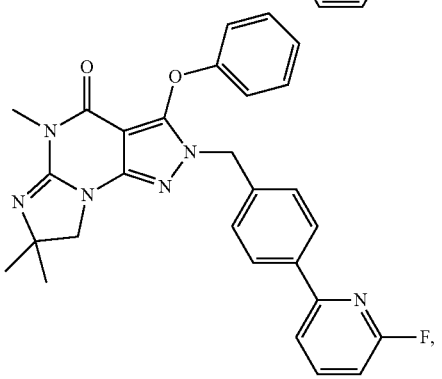

in free or salt form.

* * * * *